US011317971B2

(12) United States Patent
Crawford

(10) Patent No.: US 11,317,971 B2
(45) Date of Patent: May 3, 2022

(54) SYSTEMS AND METHODS RELATED TO ROBOTIC GUIDANCE IN SURGERY

(71) Applicant: GLOBUS MEDICAL, INC., Audubon, PA (US)

(72) Inventor: Neil R. Crawford, Chandler, AZ (US)

(73) Assignee: Globus Medical, Inc., Audubon, PA (US)

(*) Notice: Subject to any disclaimer, the term of this patent is extended or adjusted under 35 U.S.C. 154(b) by 1029 days.

(21) Appl. No.: 15/975,846

(22) Filed: May 10, 2018

(65) Prior Publication Data

US 2018/0256259 A1  Sep. 13, 2018

Related U.S. Application Data

(63) Continuation-in-part of application No. 15/609,334, filed on May 31, 2017, which is a continuation-in-part (Continued)

(51) Int. Cl.
*A61B 34/10* (2016.01)
*A61B 34/20* (2016.01)
(Continued)

(52) U.S. Cl.
CPC ............... *A61B 34/10* (2016.02); *A61B 6/12* (2013.01); *A61B 6/461* (2013.01); *A61B 6/505* (2013.01);
(Continued)

(58) Field of Classification Search
CPC .......... G06T 7/0012; G06T 7/33; G06T 7/20; G06T 7/50; G06T 7/70; G06T 19/006;
(Continued)

(56) References Cited

U.S. PATENT DOCUMENTS

| 4,150,293 A | 4/1979 | Franke |
| 5,020,933 A | 6/1991 | Salvestro et al. |

(Continued)

FOREIGN PATENT DOCUMENTS

| CN | 1536975 A | 10/2004 |
| CN | 202027725 U | 11/2011 |

(Continued)

OTHER PUBLICATIONS

US 8,231,638 B2, 07/2012, Swarup et al. (withdrawn)

(Continued)

*Primary Examiner* — Peter Luong

(57) ABSTRACT

A surgical implant planning computer positions an implant device relative to a bone of a patient. An initial image of a bone is obtained. An initial location data structure is obtained that contains data defining mapping between locations on the implant device and corresponding locations relative to the bone in the initial image. A target image of the bone of the patient is obtained. A transformation matrix is generated that transforms a contour of a portion of the bone in the initial image to satisfy a defined rule for conforming to a contour of a corresponding portion of the bone in the target image. A transformed location data structure is generated based on applying the transformation matrix to the initial location data structure. A graphical representation of the implant device is displayed overlaid at locations on the target image of the bone determined based on the transformed location data structure.

20 Claims, 28 Drawing Sheets

Related U.S. Application Data of application No. 15/157,444, filed on May 18, 2016, which is a continuation-in-part of application No. 15/095,883, filed on Apr. 11, 2016, now Pat. No. 10,893,912, which is a continuation-in-part of application No. 14/062,707, filed on Oct. 24, 2013, now Pat. No. 10,357,184, which is a continuation-in-part of application No. 13/924,505, filed on Jun. 21, 2013, now Pat. No. 9,782,229.

(60) Provisional application No. 62/615,492, filed on Jan. 10, 2018, provisional application No. 61/800,527, filed on Mar. 15, 2013, provisional application No. 61/662,702, filed on Jun. 21, 2012.

(51) Int. Cl.

| | | |
|---|---|---|
| *G06T 19/20* | (2011.01) | |
| *A61B 34/30* | (2016.01) | |
| *A61B 17/70* | (2006.01) | |
| *G06T 19/00* | (2011.01) | |
| *A61B 6/00* | (2006.01) | |
| *G06T 7/33* | (2017.01) | |
| *A61B 6/12* | (2006.01) | |
| *G06T 7/00* | (2017.01) | |
| *A61B 17/86* | (2006.01) | |
| *A61B 90/00* | (2016.01) | |
| *G06T 7/20* | (2017.01) | |
| *G06T 7/70* | (2017.01) | |
| *G06T 7/50* | (2017.01) | |
| *A61B 17/17* | (2006.01) | |
| *A61F 2/46* | (2006.01) | |
| *A61B 17/00* | (2006.01) | |
| *A61B 90/11* | (2016.01) | |

(52) U.S. Cl.
CPC ........ *A61B 6/5217* (2013.01); *A61B 17/7082* (2013.01); *A61B 34/20* (2016.02); *A61B 34/30* (2016.02); *G06T 7/0012* (2013.01); *G06T 7/33* (2017.01); *G06T 19/006* (2013.01); *G06T 19/20* (2013.01); *A61B 6/4405* (2013.01); *A61B 6/468* (2013.01); *A61B 17/1757* (2013.01); *A61B 17/7001* (2013.01); *A61B 17/86* (2013.01); *A61B 90/11* (2016.02); *A61B 2017/00477* (2013.01); *A61B 2017/00876* (2013.01); *A61B 2034/102* (2016.02); *A61B 2034/104* (2016.02); *A61B 2034/105* (2016.02); *A61B 2034/107* (2016.02); *A61B 2034/2051* (2016.02); *A61B 2034/2055* (2016.02); *A61B 2034/2068* (2016.02); *A61B 2090/033* (2016.02); *A61B 2090/363* (2016.02); *A61B 2090/376* (2016.02); *A61B 2090/3762* (2016.02); *A61B 2090/3945* (2016.02); *A61B 2090/3966* (2016.02); *A61B 2090/3983* (2016.02); *A61F 2/4611* (2013.01); *A61F 2002/4632* (2013.01); *G06T 7/20* (2013.01); *G06T 7/50* (2017.01); *G06T 7/70* (2017.01); *G06T 19/003* (2013.01); *G06T 2200/24* (2013.01); *G06T 2207/10081* (2013.01); *G06T 2207/10088* (2013.01); *G06T 2207/10116* (2013.01); *G06T 2207/30008* (2013.01); *G06T 2207/30204* (2013.01); *G06T 2207/30241* (2013.01); *G06T 2210/41* (2013.01); *G06T 2219/2016* (2013.01)

(58) Field of Classification Search
CPC .................. G06T 19/20; G06T 19/003; G06T 2200/24; G06T 2207/10081; G06T 2207/10088; G06T 2207/10116; G06T 2207/30008; G06T 2207/30204; G06T 2207/30241; G06T 2210/41; G06T 2219/2016; A61F 2/4611; A61F 2002/4632; G16H 50/30

See application file for complete search history.

(56) References Cited

U.S. PATENT DOCUMENTS

| | | |
|---|---|---|
| 5,246,010 A | 9/1993 | Gazzara et al. |
| 5,354,314 A | 10/1994 | Hardy et al. |
| 5,397,323 A | 3/1995 | Taylor et al. |
| 5,483,961 A * | 1/1996 | Kelly ............... A61B 90/10 |
| | | 600/417 |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |

(56) References Cited

U.S. PATENT DOCUMENTS

| | | |
|---|---|---|
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,207,995 B1 | 4/2007 | Vandewalle |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |

(56) References Cited

U.S. PATENT DOCUMENTS

| | | |
|---|---|---|
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,126,234 B1 * | 2/2012 | Edwards .......... G06T 19/20 382/128 |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,313,430 B1 | 11/2012 | Pimenta |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |

(56) References Cited

U.S. PATENT DOCUMENTS

| | | |
|---|---|---|
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Fang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Tott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,463,073 B2 | 10/2016 | Gill et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 10,575,906 B2 | 3/2020 | Wu |
| 2001/0036302 A1 | 11/2001 | Miller |
| 2002/0035321 A1 | 3/2002 | Bucholz et al. |
| 2003/0161442 A1 | 8/2003 | Zeiss |
| 2004/0019263 A1 | 1/2004 | Jutras et al. |
| 2004/0024311 A1 | 2/2004 | Quaid |
| 2004/0034302 A1 | 2/2004 | Abovitz et al. |
| 2004/0068172 A1 | 4/2004 | Nowinski et al. |
| 2004/0076259 A1 | 4/2004 | Jensen et al. |
| 2004/0157188 A1 | 8/2004 | Luth et al. |
| 2005/0085714 A1 | 4/2005 | Foley et al. |
| 2005/0096502 A1 | 5/2005 | Khalili |
| 2005/0107679 A1 | 5/2005 | Geiger et al. |
| 2005/0119639 A1 | 6/2005 | McCombs et al. |
| 2005/0143651 A1 | 6/2005 | Verard et al. |
| 2005/0149045 A1 | 7/2005 | Elliott |
| 2005/0171558 A1 | 8/2005 | Abovitz et al. |
| 2005/0215888 A1 | 9/2005 | Grimm et al. |
| 2006/0036264 A1 | 2/2006 | Selover et al. |
| 2006/0100610 A1 | 5/2006 | Wallace et al. |
| 2006/0142657 A1 | 6/2006 | Quaid et al. |
| 2006/0173329 A1 | 8/2006 | Marquart et al. |
| 2006/0178559 A1 | 8/2006 | Kumar et al. |
| 2006/0184396 A1 | 8/2006 | Dennis et al. |
| 2006/0241416 A1 | 10/2006 | Marquart et al. |
| 2006/0264963 A1 | 11/2006 | Reed et al. |
| 2006/0291612 A1 | 12/2006 | Nishide et al. |
| 2007/0001879 A1 | 1/2007 | Kaftan et al. |
| 2007/0015987 A1 | 1/2007 | Benlloch Baviera et al. |
| 2007/0016009 A1 | 1/2007 | Lakin et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0122020 A1 | 5/2007 | Claus et al. |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2007/0238985 A1 | 10/2007 | Smith et al. |
| 2008/0004523 A1 | 1/2008 | Jensen |
| 2008/0010706 A1 | 1/2008 | Moses et al. |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0119725 A1 | 5/2008 | Lloyd |
| 2008/0144906 A1 | 6/2008 | Allred et al. |
| 2008/0154389 A1 | 6/2008 | Smith et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0188934 A1 | 8/2008 | Moser et al. |
| 2008/0200794 A1 | 8/2008 | Teichman et al. |
| 2008/0214922 A1 | 9/2008 | Hartmann et al. |
| 2008/0228068 A1 | 9/2008 | Viswanathan et al. |
| 2008/0228195 A1 | 9/2008 | von Jako et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0099445 A1 | 4/2009 | Burger |
| 2009/0185655 A1 | 7/2009 | Koken et al. |
| 2009/0198121 A1 | 8/2009 | Hoheisel |
| 2009/0216113 A1 | 8/2009 | Meier et al. |

(56) References Cited

U.S. PATENT DOCUMENTS

| | | |
|---|---|---|
| 2009/0228019 A1 | 9/2009 | Gross et al. |
| 2009/0234217 A1 | 9/2009 | Mire et al. |
| 2009/0240141 A1 | 9/2009 | Neubauer et al. |
| 2009/0254326 A1 | 10/2009 | Isaacs |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2009/0306480 A1 | 12/2009 | Protopsaltis |
| 2009/0306499 A1 | 12/2009 | Van Vorhis et al. |
| 2010/0022874 A1 | 1/2010 | Wang et al. |
| 2010/0039506 A1 | 2/2010 | Sarvestani et al. |
| 2010/0046718 A1 | 2/2010 | Weiser et al. |
| 2010/0076305 A1 | 3/2010 | Maier-Hein et al. |
| 2010/0114288 A1 | 5/2010 | Haller et al. |
| 2010/0125286 A1 | 5/2010 | Wang et al. |
| 2010/0130986 A1 | 5/2010 | Mailloux et al. |
| 2010/0174410 A1 | 7/2010 | Greer et al. |
| 2010/0228117 A1 | 9/2010 | Hartmann |
| 2010/0228265 A1 | 9/2010 | Prisco |
| 2010/0228340 A1 | 9/2010 | Erbel et al. |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0019884 A1 | 1/2011 | Blau |
| 2011/0020084 A1 | 1/2011 | Brett et al. |
| 2011/0022229 A1 | 1/2011 | Jang et al. |
| 2011/0040305 A1 | 2/2011 | Gomez et al. |
| 2011/0071347 A1 | 3/2011 | Rogers et al. |
| 2011/0077504 A1 | 3/2011 | Fischer et al. |
| 2011/0082468 A1 | 4/2011 | Hagag et al. |
| 2011/0098553 A1 | 4/2011 | Robbins et al. |
| 2011/0137152 A1 | 6/2011 | Li |
| 2011/0184245 A1 | 7/2011 | Xia et al. |
| 2011/0190588 A1 | 8/2011 | McKay |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0257653 A1 | 10/2011 | Hughes et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0289820 A1 | 11/2012 | Rohling |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0051647 A1 | 2/2013 | Miao et al. |
| 2013/0060146 A1 | 3/2013 | Yang et al. |
| 2013/0060337 A1 | 3/2013 | Petersheim et al. |
| 2013/0064427 A1 | 3/2013 | Picard et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0165948 A1 | 6/2013 | Popovic |
| 2013/0178867 A1 | 7/2013 | Farritor et al. |
| 2013/0178868 A1 | 7/2013 | Roh |
| 2013/0178870 A1 | 7/2013 | Schena |
| 2013/0184873 A1 | 7/2013 | Namiki |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0268007 A1 | 10/2013 | Rezach et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0279784 A1 | 10/2013 | Gill |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345718 A1 | 12/2013 | Crawford et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0052150 A1 | 2/2014 | Taylor et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088410 A1 | 3/2014 | Wu |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135744 A1 | 5/2014 | Stein et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | Grunberg |

(56) References Cited

U.S. PATENT DOCUMENTS

| | | |
|---|---|---|
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0200587 A1 | 7/2014 | Pompee et al. |
| 2014/0130810 A1 | 8/2014 | Azizian et al. |
| 2014/0221819 A1 | 8/2014 | Sarment |
| 2014/0221822 A1 | 8/2014 | Ehlers et al. |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275955 A1 | 9/2014 | Crawford et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276943 A1 | 9/2014 | Bowling et al. |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316420 A1 | 10/2014 | Ballard et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0336669 A1 | 11/2014 | Park |
| 2014/0343416 A1 | 11/2014 | Panescu et al. |
| 2014/0357989 A1 | 12/2014 | Hendriks et al. |
| 2014/0364720 A1 | 12/2014 | Darrow et al. |
| 2014/0371577 A1 | 12/2014 | Maillet et al. |
| 2015/0032164 A1 | 1/2015 | Crawford et al. |
| 2015/0039034 A1 | 2/2015 | Frankel et al. |
| 2015/0085970 A1 | 3/2015 | Bouhnik et al. |
| 2015/0100066 A1 | 4/2015 | Kostrzewski et al. |
| 2015/0146847 A1 | 5/2015 | Liu |
| 2015/0150524 A1 | 6/2015 | Yorkston et al. |
| 2015/0157416 A1 | 6/2015 | Andersson |
| 2015/0157468 A1 | 6/2015 | Wakayama et al. |
| 2015/0173810 A1 | 6/2015 | Biedermann et al. |
| 2015/0196261 A1 | 7/2015 | Funk |
| 2015/0196365 A1 | 7/2015 | Kostrzewski et al. |
| 2015/0209056 A1 | 7/2015 | Shoham et al. |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0063707 A1 | 3/2016 | Masumoto |
| 2016/0166329 A1 | 6/2016 | Langan et al. |
| 2016/0235480 A1 | 8/2016 | Scholl et al. |
| 2016/0235492 A1 | 8/2016 | Morard et al. |
| 2016/0235493 A1 | 8/2016 | Leboeuf, II et al. |
| 2016/0249990 A1 | 9/2016 | Glozman et al. |
| 2016/0256225 A1 | 9/2016 | Crawford et al. |
| 2016/0296266 A1 | 10/2016 | Chandanson et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0007327 A1 | 1/2017 | Haider et al. |
| 2017/0079727 A1 | 3/2017 | Crawford et al. |
| 2017/0112552 A1 | 4/2017 | Sinnott et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0209222 A1 | 7/2017 | Gassner et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0245946 A1 | 8/2017 | Tabandeh et al. |
| 2017/0258426 A1 | 9/2017 | Risher-Kelly et al. |
| 2017/0258526 A1 | 9/2017 | Lang |
| 2017/0258535 A1 | 9/2017 | Crawford et al. |
| 2017/0265952 A1 | 9/2017 | Donhowe et al. |
| 2017/0273748 A1 | 9/2017 | Hourtash et al. |
| 2017/0296277 A1 | 10/2017 | Hourtash et al. |
| 2017/0312032 A1 | 11/2017 | Amanatullah et al. |
| 2017/0333137 A1 | 11/2017 | Roessler |
| 2017/0348061 A1 | 12/2017 | Joshi et al. |
| 2017/0360493 A1 | 12/2017 | Zucher et al. |
| 2018/0008355 A1 | 1/2018 | Mozes et al. |
| 2018/0042464 A1 | 2/2018 | Arai et al. |
| 2018/0049825 A1 | 2/2018 | Kwon et al. |
| 2018/0064496 A1 | 3/2018 | Hladio et al. |
| 2018/0064497 A1 | 3/2018 | Hussain et al. |
| 2018/0066794 A1 | 3/2018 | Okuda et al. |
| 2018/0200016 A1 | 7/2018 | Chappuis |
| 2018/0249981 A1 | 9/2018 | Johnson et al. |
| 2018/0325610 A1 | 11/2018 | Cameron et al. |

FOREIGN PATENT DOCUMENTS

| | | |
|---|---|---|
| CN | 102596062 A | 7/2012 |
| CN | 102612350 A | 7/2012 |
| CN | 102933163 A | 2/2013 |
| CN | 104994805 A | 10/2015 |
| CN | 106163446 A | 11/2016 |
| CN | 209153975 U | 7/2019 |
| DE | 102014221469 A1 | 4/2016 |
| EP | 1103223 A2 | 5/2001 |
| EP | 1346687 A1 | 9/2003 |
| EP | 1523950 A1 | 4/2005 |
| EP | 2471483 A1 | 7/2012 |
| EP | 3181085 A1 | 6/2017 |
| EP | 3517069 A1 | 7/2019 |
| JP | 3-118053 A | 5/1991 |
| JP | 11-313837 A | 11/1999 |
| JP | 2001135734 A | 5/2001 |
| JP | 2002253574 A | 9/2002 |
| JP | 2004518475 A | 6/2004 |
| JP | 2005-533579 A | 11/2005 |
| JP | 2007-044488 A | 2/2007 |
| JP | 2007-531543 A | 11/2007 |
| JP | 2007534351 A | 11/2007 |
| JP | 2007537835 A | 12/2007 |
| JP | 2008-507361 A | 3/2008 |
| JP | 2008188417 A | 8/2008 |
| JP | 2008-538184 A | 10/2008 |
| JP | 2009537229 A | 10/2009 |
| JP | 2011-120782 A | 6/2011 |
| JP | 2011-517594 A | 6/2011 |
| JP | 2012075507 A | 4/2012 |
| JP | 2013-541365 A | 11/2013 |
| JP | 2014036700 A | 2/2014 |
| JP | 2014097220 A | 5/2014 |
| JP | 2015-504721 A | 2/2015 |
| JP | 201536161 A | 2/2015 |
| JP | 2015100677 A | 6/2015 |
| JP | 2015119968 A | 7/2015 |
| JP | 2015521084 A | 7/2015 |
| JP | 2015528713 A | 10/2015 |
| JP | 2015-534480 A | 12/2015 |
| JP | 2016043211 A | 4/2016 |
| JP | 2016185225 A | 10/2016 |
| JP | 2016-193222 A | 11/2016 |
| JP | 2016193222 A | 11/2016 |
| JP | 2016539681 A | 12/2016 |
| JP | 2017087313 A | 5/2017 |
| JP | 2017176848 A | 10/2017 |
| JP | 2017530842 A | 10/2017 |
| JP | 2017223657 A | 12/2017 |
| JP | 2018011938 A | 1/2018 |
| JP | 2018-027288 A | 2/2018 |
| JP | 2018516107 A | 6/2018 |
| JP | 2018-114283 A | 7/2018 |

(56) References Cited

FOREIGN PATENT DOCUMENTS

| | | |
|---|---|---|
| JP | 2018523516 A | 8/2018 |
| JP | 2018-202156 A | 12/2018 |
| WO | 03007198 A2 | 1/2003 |
| WO | 2005039417 A1 | 5/2005 |
| WO | 2009092164 A1 | 7/2009 |
| WO | 2009126953 A2 | 10/2009 |
| WO | 2011128766 A2 | 10/2011 |
| WO | 2012050634 A1 | 4/2012 |
| WO | 2013114823 A1 | 8/2013 |
| WO | 2013192598 A1 | 12/2013 |
| WO | 2014010760 A1 | 1/2014 |
| WO | 2014139023 A1 | 9/2014 |
| WO | 2015023665 A1 | 2/2015 |
| WO | 2015052718 A1 | 4/2015 |
| WO | 2015061638 A1 | 4/2015 |
| WO | 2015079775 A1 | 6/2015 |
| WO | 2015142762 A1 | 9/2015 |
| WO | 201613049 A1 | 1/2016 |
| WO | 2016087539 A2 | 6/2016 |
| WO | 2016114834 A2 | 7/2016 |
| WO | 2016152255 A1 | 9/2016 |
| WO | 2016170372 A1 | 10/2016 |
| WO | 2017221257 A1 | 2/2017 |
| WO | 2017127202 A1 | 7/2017 |
| WO | 2017147596 A1 | 8/2017 |
| WO | 2017186799 A1 | 11/2017 |
| WO | 2017204832 A1 | 11/2017 |
| WO | 2018183461 A1 | 10/2018 |

OTHER PUBLICATIONS

Markelj et al.: "A review of 3D/2D registration methods for image-guided interventions", Medical Image Analysis, Oxford University Press, Oxford, GB, vol. 16, No. 3,pp. 642-661, Apr. 1, 2012.

Gong Ren Hui et al.: "Interactive initialization of 2D/3D rigid registration", Medical Physics, AIP, Melville, NY, US, vol. 40, No. 12, 14 pages, Dec. 2013.

Dumenil A et al.: "A versatile intensity-based 3D/2D rigid registration compatible with mobile C-arm for endovascular treatment of abdominal aortic aneurysm", International Journal of Computer Assisted Radiology and Surgery, Springer, DE, vol. 11, No. 9, pp. 1713-1729, May 26, 2016.

Alk et al., "Smart Device Assisted Method for Rod Length and Rod Radius Measurement in Percutaneious Pedicle Screw Surgery", Prizeglad Elektrotechniczny, vol. 3, Mar. 5, 2016, pp. 30-33.

Marintschev et al.: "Navigation of vertebra-pelvic fixations based on CT-fluoro macthing", European Spine Journal, Springer, Berlin, DE, vol. 19, No. 11, pp. 1921-1927, Jun. 16, 2010.

* cited by examiner

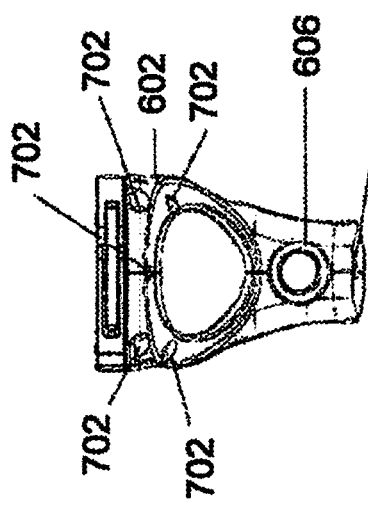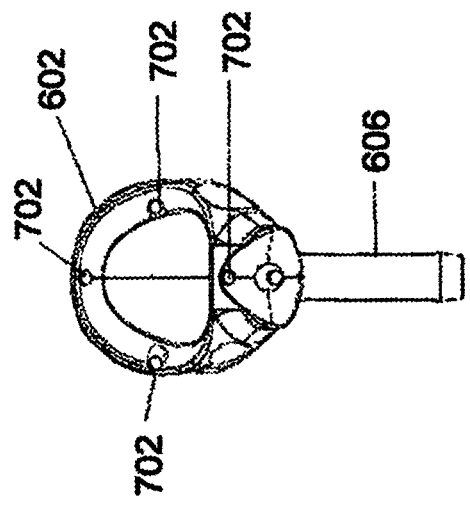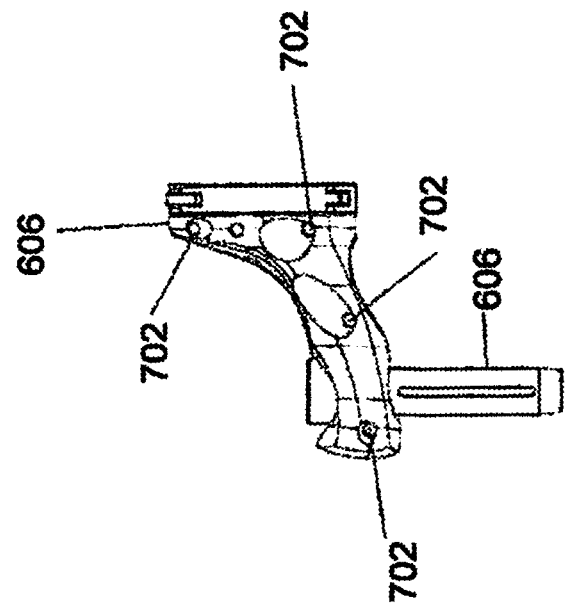

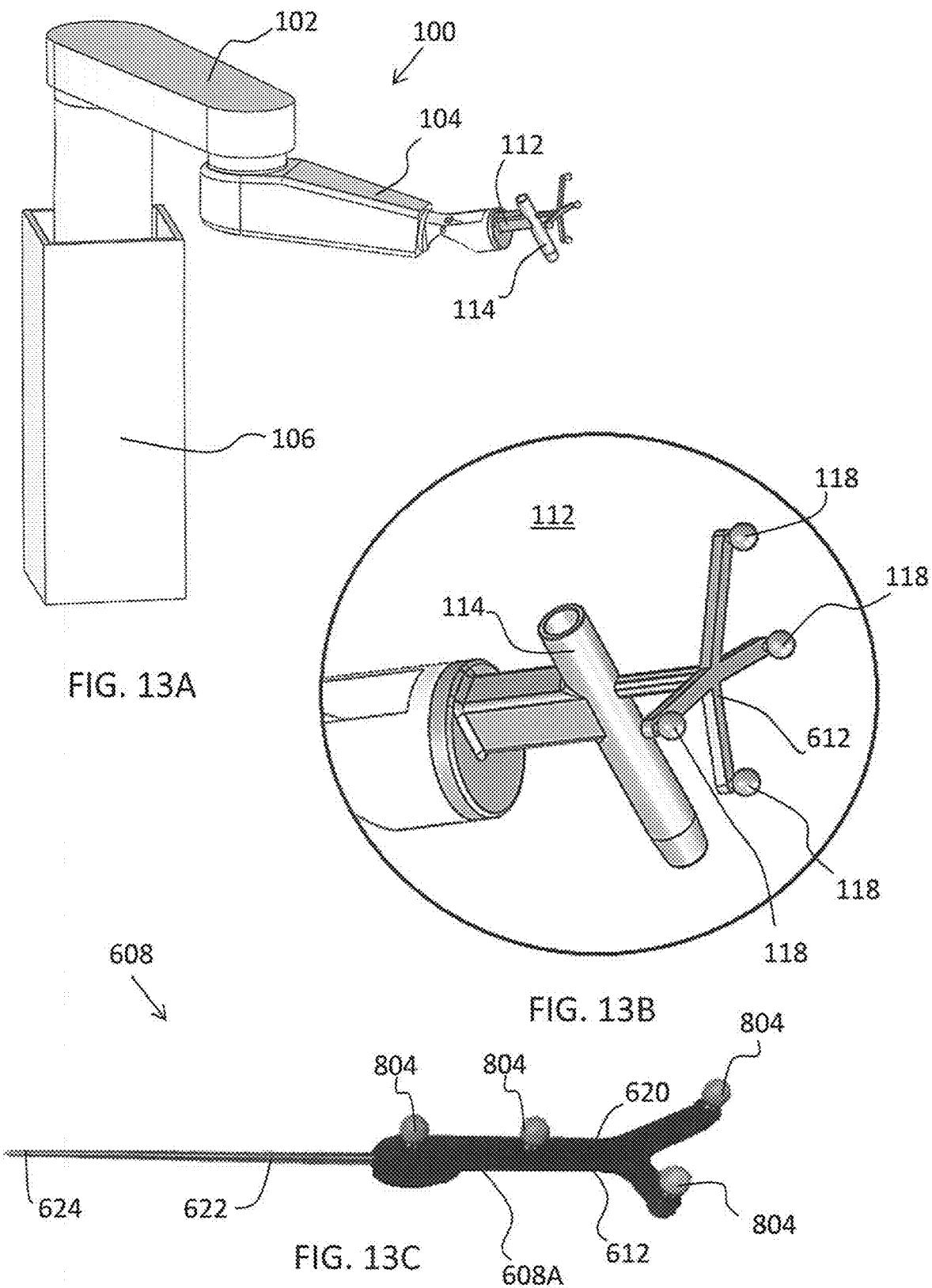

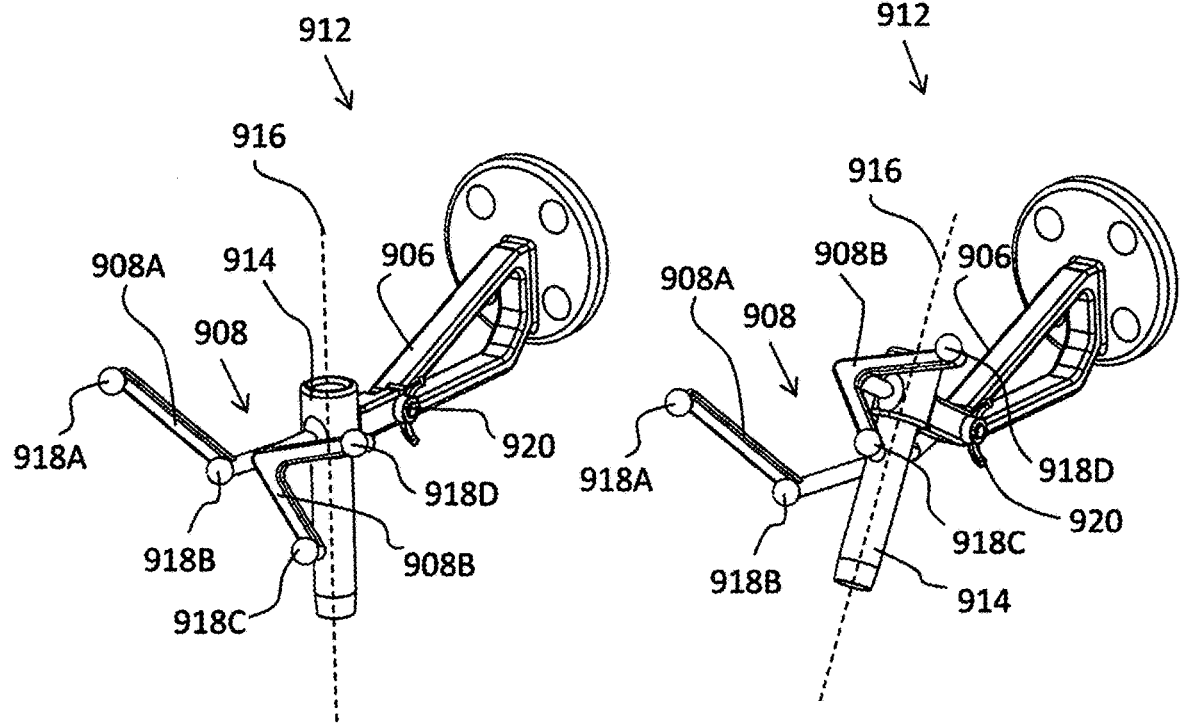
FIG. 14A  FIG. 14B
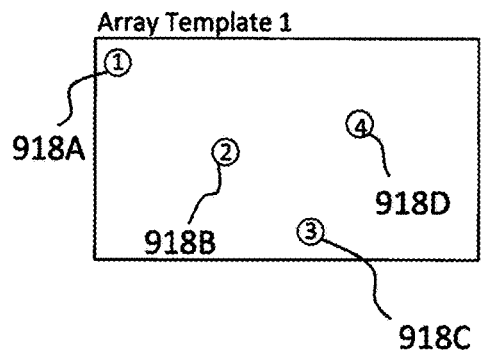 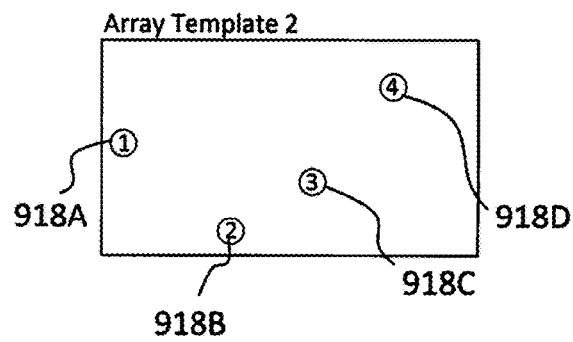
FIG. 14C  FIG. 14D

SYSTEMS AND METHODS RELATED TO ROBOTIC GUIDANCE IN SURGERY

CROSS-REFERENCE TO RELATED APPLICATIONS

This application is a continuation-in-part application of U.S. patent application Ser. No. 15/609,334 filed on May 31, 2017 which is continuation-in-part of U.S. patent application Ser. No. 15/157,444 filed on May 18, 2016, which is a continuation in part of U.S. patent application Ser. No. 15/095,883, filed Apr. 11, 2016, which is a continuation-in-part of U.S. patent application Ser. No. 14/062,707, filed on Oct. 24, 2013, which is a continuation-in-part application of U.S. patent application Ser. No. 13/924,505, filed on Jun. 21, 2013, which claims priority to provisional application No. 61/662,702 filed on Jun. 21, 2012 and claims priority to provisional application No. 61/800,527 filed on Mar. 15, 2013, and claims priority to provisional application 62/615,492 filed on Jan. 10, 2018, which are incorporate in their entirety herein.

FIELD OF THE INVENTION

The present disclosure relates to medical devices, and more particularly, surgical robotic systems and related methods and devices.

BACKGROUND

Position recognition systems for robot assisted surgeries are used to determine the position of and track a particular object in 3-dimensions (3D). In robot assisted surgeries, for example, certain objects, such as surgical instruments, need to be tracked with a high degree of precision as the instrument is being positioned and moved by a robot or by a physician, for example.

Infrared signal based position recognition systems may use passive and/or active sensors or markers for tracking the objects. In passive sensors or markers, objects to be tracked may include passive sensors, such as reflective spherical balls, which are positioned at strategic locations on the object to be tracked. Infrared transmitters transmit a signal, and the reflective spherical balls reflect the signal to aid in determining the position of the object in 3D. In active sensors or markers, the objects to be tracked include active infrared transmitters, such as light emitting diodes (LEDs), and thus generate their own infrared signals for 3D detection.

With either active or passive tracking sensors, the system then geometrically resolves the 3-dimensional position of the active and/or passive sensors based on information from or with respect to one or more of the infrared cameras, digital signals, known locations of the active or passive sensors, distance, the time it took to receive the responsive signals, other known variables, or a combination thereof.

Position feedback is thereby used to precisely guide movement of robotic arms and tools relative to a patients' surgical site. Currently, development of a surgical plan for the desired locations where screws, tools, or other surgical implant devices are to be implanted when using a surgical robot is performed manually by a surgeon. A surgeon analyzes a patient's medical image and may mark up the image to create a surgical plan. Although each patient is different, they share many similarities. Therefore, the process of marking up an image to create a surgical plan need not start from scratch for each case. These surgical systems could benefit from a more automated, rapid and accurate process of planning of the characteristics of a surgical implant device that is to be implanted into a particular bone and planning of the precise location, angle of entry, and depth of implantation of the device. Such a process could be based on successful surgical plans created for previous patients.

SUMMARY

Various embodiments of the present disclosure are directed to a surgical system that allows auto-generation of a surgical plan and/or enables a surgeon to develop a surgical plan for implanting a surgical implant device with respect to a bone shown in one medical image, and that automatically transforms the surgical plan for use in implanting the surgical implant device into a bone that is shown in another medical image. In some embodiments, a surgeon can plan implantation of the implant device relative to an initial image of a bone, which may correspond to an earlier image of this or another patient or may correspond to a general surgical bone model. When a target image of the patient's bone is then obtained, such as during surgery or preparation, the surgical system can generate a transformation matrix related to transforming one or more bone contours shown in the initial image to conform to corresponding one or more bone contours in the target image. The surgical system then uses the transformation matrix to transform the surgical plan that was developed relative to the initial image to now be relative to the target image. The location, angle of entry, and depth of implantation of the implant device and/or sizing of the implantation device that was earlier specified with respect to the bone shown in the initial image can thereby be transformed relative to the bone shown in the target image. The transformed surgical plan can be displayed for review by the surgeon and/or can be provided to a surgical robotic system to control positioning of a surgical end-effector of the surgical robotic system relative to the bone of the patient.

According to some embodiments of inventive concepts, a method is provided to operate a surgical implant planning computer for positioning a surgical implant device relative to a bone of a patient. An initial image of a bone is obtained. An initial location data structure is obtained that contains data defining mapping between a set of locations on the surgical implant device and a corresponding set of locations relative to the bone in the initial image. A target image of the bone of the patient is obtained. A transformation matrix is generated that transforms a contour of a portion of the bone in the initial image to satisfy a defined rule for conforming to a contour of a corresponding portion of the bone in the target image. A transformed location data structure is generated based on applying the transformation matrix to the initial location data structure. A graphical representation of the surgical implant device is displayed overlaid at locations on the target image of the bone determined based on the transformed location data structure.

In some further embodiments, the transformed location data structure is provided to a surgical robotic system to control positioning of a surgical end-effector of the surgical robotic system relative to a location on the bone of the patient based on data of the transformed location data structure. Locations that are defined by the transformed location data structure in a reference coordinate system of the target image of the bone can be transformed to another reference coordinate system of the surgical end-effector. Movement of the surgical end-effector by the surgical robotic system to position the surgical end-effector relative to the location on the bone of the patient can be controlled based on the transformed locations to facilitate implantation of the surgical implant device in the bone of the patient.

Corresponding surgical implant planning computers, surgical systems, and computer program products are disclosed.

Still other methods and corresponding surgical implant planning computers, surgical systems, and computer program products according to embodiments of the inventive subject matter will be or become apparent to one with skill in the art upon review of the following drawings and detailed description. It is intended that all such methods, surgical implant planning computers, surgical systems, and computer program products be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings:

FIGS. 7A-7C illustrate an end-effector in accordance with an exemplary embodiment;

FIG. 13A illustrates a portion of a robot including the robot arm and an end-effector in accordance with an exemplary embodiment;

FIG. 13B is a close-up view of the end-effector, with a plurality of tracking markers rigidly affixed thereon, shown in FIG. 13A;

FIG. 13C is a tool or instrument with a plurality of tracking markers rigidly affixed thereon according to one embodiment;

FIG. 14A is an alternative version of an end-effector with moveable tracking markers in a first configuration;

FIG. 14B is the end-effector shown in FIG. 14A with the moveable tracking markers in a second configuration;

FIG. 14C shows the template of tracking markers in the first configuration from FIG. 14A;

FIG. 14D shows the template of tracking markers in the second configuration from FIG. 14B;

DETAILED DESCRIPTION

Figure 1:
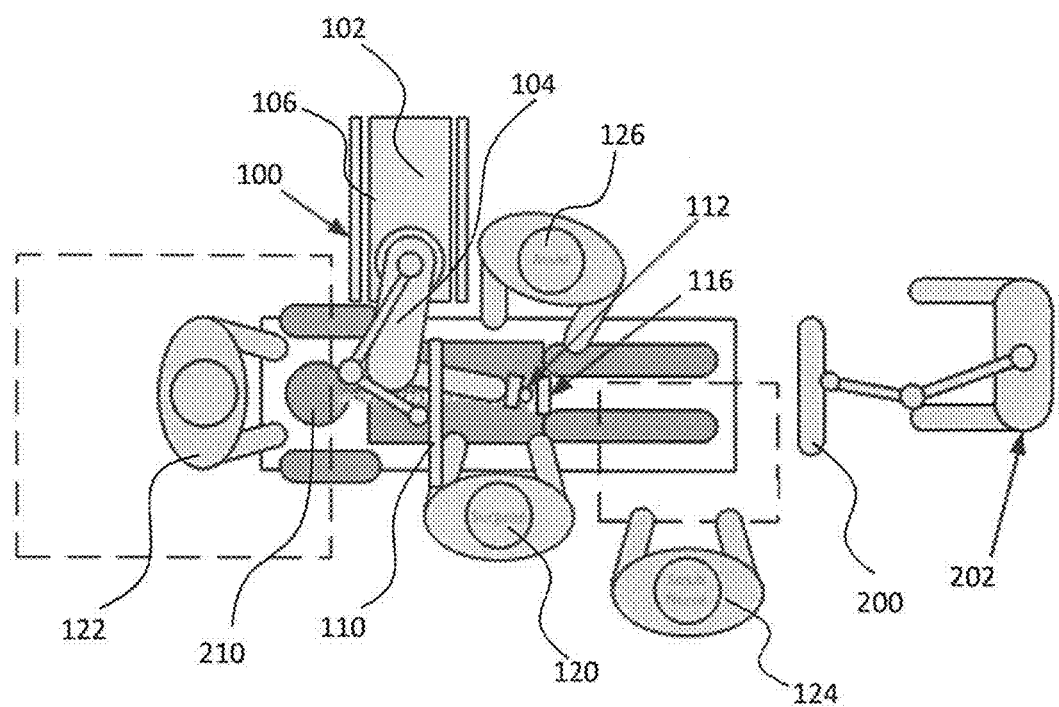
FIG. 1 is an overhead view of a potential arrangement for locations of the robotic system, patient, surgeon, and other medical personnel during a surgical procedure.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

As explained above, a surgeon may develop a surgical plan by analyzing a patient's medical image and marking up the image to create the surgical plan for desired locations where screws, tools, or other surgical implant devices are to be implanted when using a surgical robot that assists with implanting the devices. When using a surgical robotic system, a desired screw location may be planned preoperatively using a computerized interface. In this interface, the surgeon scrolls through or otherwise manipulates views of the patient's medical images, such as CT scan, x-ray, or MRI and positions graphic objects representing the desired locations of screws as overlays on a displayed medical image of a bone. The system stores the planned screw locations in system memory, typically by storing the x,y,z Cartesian coordinates of the tip and tail locations of each screw in the coordinate system of the volumetric scan of the medical image, or in the case of fluoroscopic guidance, saving tip and tail location coordinates in the coordinate system through which the fluoro shot images are projected. Later, when the robot is activated, the coordinate system in which the screw locations have been planned is registered with the coordinate system of the tracking cameras and the robot moves to the planned locations, holding a guide tube for preparation of screw holes and insertion of screws.

In accordance with various embodiments disclosed herein, the surgical planning process is improved by providing a surgical implant planning computer that automatically predicts desired locations of screws and/or other surgical implant devices before the surgeon views the patient's images and can incorporate the surgeon's preferences regarding screw or other device placement (preferred depth, preferred angle, etc.) into an automatic predictive surgical plan with respect to an initial medical image. Alternatively or additionally, the surgical implant planning computer obtains an initial surgical plan developed by a surgeon for implanting a screw or other implant device with respect to the initial medical image. The system transforms the automatic predictive surgical plan and/or the surgeon's initial surgical plan made with respect to the initial medical image to a transformed plan for use in implanting the surgical implant device into a bone that is shown in a target medical image. Such automatic planning can reduce the time required for the surgery and increase precision of planning.

Although various embodiments are described in the context of developing a surgical plan for implanting screws into a bone, this disclosure is not limited thereto. Embodiments disclosed herein can be used to plan the implantation of any type of surgical implant device into a bone, tissue, cartilage, or other anatomical structure.

An example surgical robotic system is initially described below in detail followed by a description of various configurations and operations of a surgical implant planning computer as part of a surgical system in accordance with embodiments of the present disclosure.

Surgical Robotic System

Figure 2:
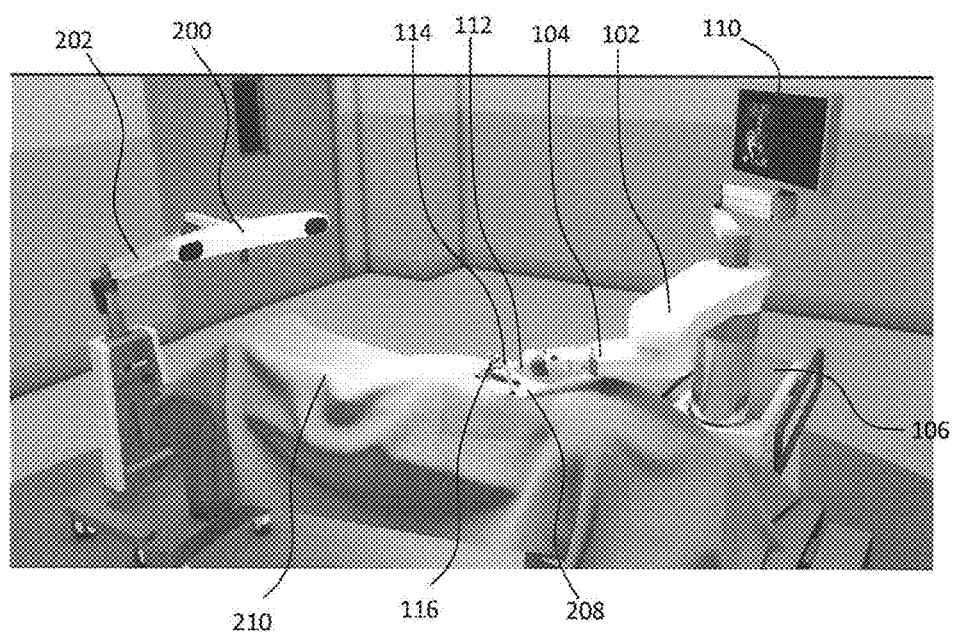
FIG. 2 illustrates the robotic system including positioning of the surgical robot and the camera relative to the patient according to one embodiment.

Turning now to the drawing, FIGS. 1 and 2 illustrate a surgical robot system 100 in accordance with an exemplary embodiment. Surgical robot system 100 may include, for example, a surgical robot 102, one or more robot arms 104, a base 106, a display 110, an end-effector 112, for example, including a guide tube 114, and one or more tracking markers 118. The surgical robot system 100 may include a patient tracking device 116 also including one or more tracking markers 118, which is adapted to be secured directly to the patient 210 (e.g., to a bone of the patient 210). The surgical robot system 100 may also use a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetrical cameras), able to identify, for example, active and passive tracking markers 118 (shown as part of patient tracking device 116 in FIG. 2 and shown by enlarged view in FIGS. 13A-13B) in a given measurement volume viewable from the perspective of the camera 200. The camera 200 may scan the given measurement volume and detect the light that comes from the markers 118 in order to identify and determine the position of the markers 118 in three-dimensions. For example, active markers 118 may include infrared-emitting markers that are activated by an electrical signal (e.g., infrared light emitting diodes (LEDs)), and/or passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 may remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End-effector 112 may be coupled to the robot arm 104 and controlled by at least one motor. In exemplary embodiments, end-effector 112 can comprise a guide tube 114, which is able to receive and orient a surgical instrument 608 (described further herein) used to perform surgery on the patient 210. As used herein, the term "end-effector" is used interchangeably with the terms "end-effectuator" and "effectuator element." Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively controlled). In some exemplary embodiments, selective control of the translation and orientation of end-effector 112 can permit performance of medical procedures with significantly improved accuracy compared to conventional robots that use, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end-effector 112 and/or the surgical instrument 608. Thus, in use, in exemplary embodiments, a physician or other user can operate the system 100, and has the option to stop, modify, or manually control the autonomous movement of end-effector 112 and/or the surgical instrument 608. Further details of surgical robot system 100 including the control and movement of a surgical instrument 608 by surgical robot 102 can be found in co-pending U.S. patent application Ser. No. 13/924,505, which is incorporated herein by reference in its entirety.

The robotic surgical system 100 can comprise one or more tracking markers 118 configured to track the movement of robot arm 104, end-effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, and/or on the end-effector 112. In exemplary embodiments, at least one tracking marker 118 of the plurality of tracking markers 118 can be mounted or otherwise secured to the end-effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screw driver, dilator, implant inserter, or the like). Thus, the tracking markers 118 enable each of the marked objects (e.g., the end-effector 112, the patient 210, and the surgical tools 608) to be tracked by the robot 102. In exemplary embodiments, system 100 can use tracking information collected from each of the marked objects to calculate the orientation and location, for example, of the end-effector 112, the surgical instrument 608 (e.g., positioned in the tube 114 of the end-effector 112), and the relative position of the patient 210.

The markers 118 may include radiopaque or optical markers. The markers 118 may be suitably shaped include spherical, spheroid, cylindrical, cube, cuboid, or the like. In exemplary embodiments, one or more of markers 118 may be optical markers. In some embodiments, the positioning of one or more tracking markers 118 on end-effector 112 can maximize the accuracy of the positional measurements by serving to check or verify the position of end-effector 112. Further details of surgical robot system 100 including the control, movement and tracking of surgical robot 102 and of a surgical instrument 608 can be found in U.S. patent publication No. 2016/0242849, which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end-effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end-effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
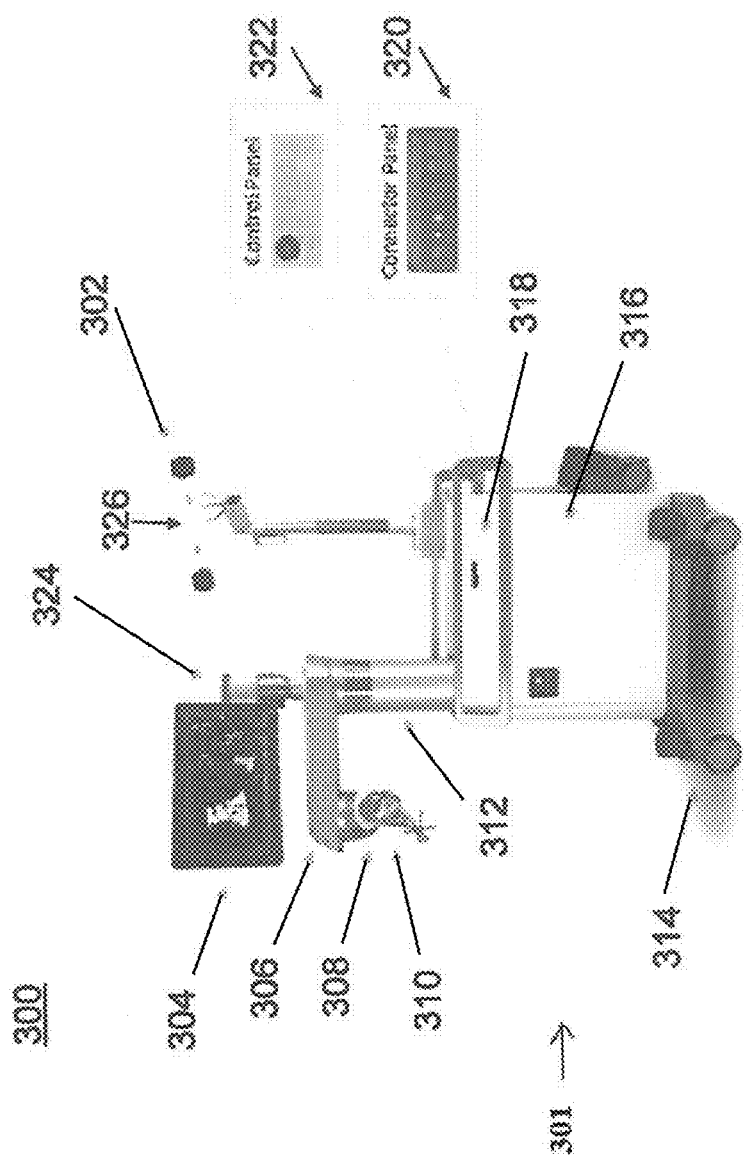
FIG. 3 illustrates a surgical robotic system in accordance with an exemplary embodiment.

Similar to surgical robot system 100, FIG. 3 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end-effector 310, vertical column 312, casters 314, cabinet 316, tablet drawer 318, connector panel 320, control panel 322, and ring of information 324. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 1 and 2.

Figure 4:
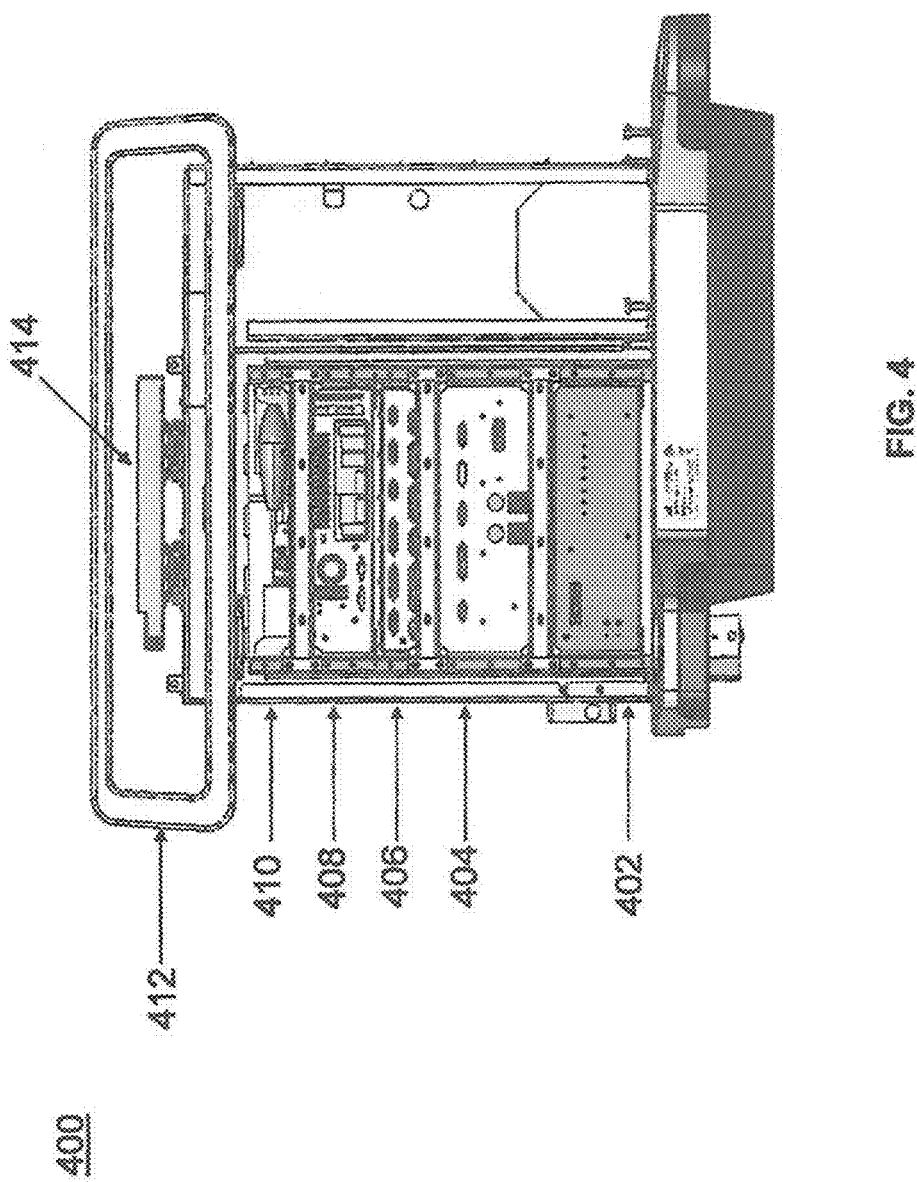
FIG. 4 illustrates a portion of a surgical robot in accordance with an exemplary embodiment.

FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
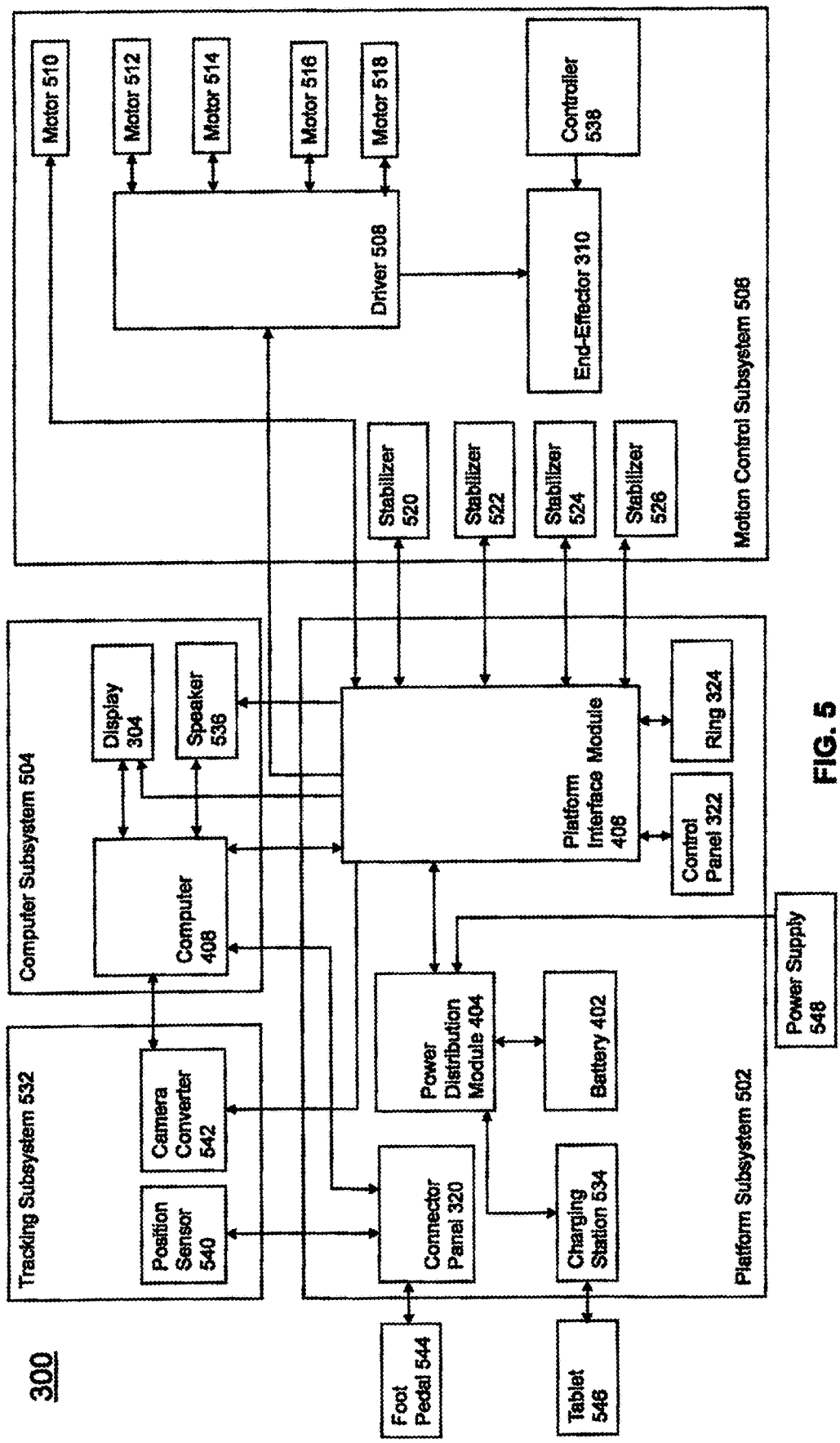
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end-effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end-effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein.

Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure.

Motion control subsystem 506 may be configured to physically move vertical column 312, upper arm 306, lower arm 308, or rotate end-effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end-effector 310 in a manner such that one may control the roll and one may control the tilt, thereby providing multiple angles that end-effector 310 may be moved. These movements may be achieved by controller 538 which may control these movements through load cells disposed on end-effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on a three dimensional image of the patient's anatomy on display 304. The user may initiate this automatic movement by stepping on foot pedal 544 or some other input means.

Figure 6:
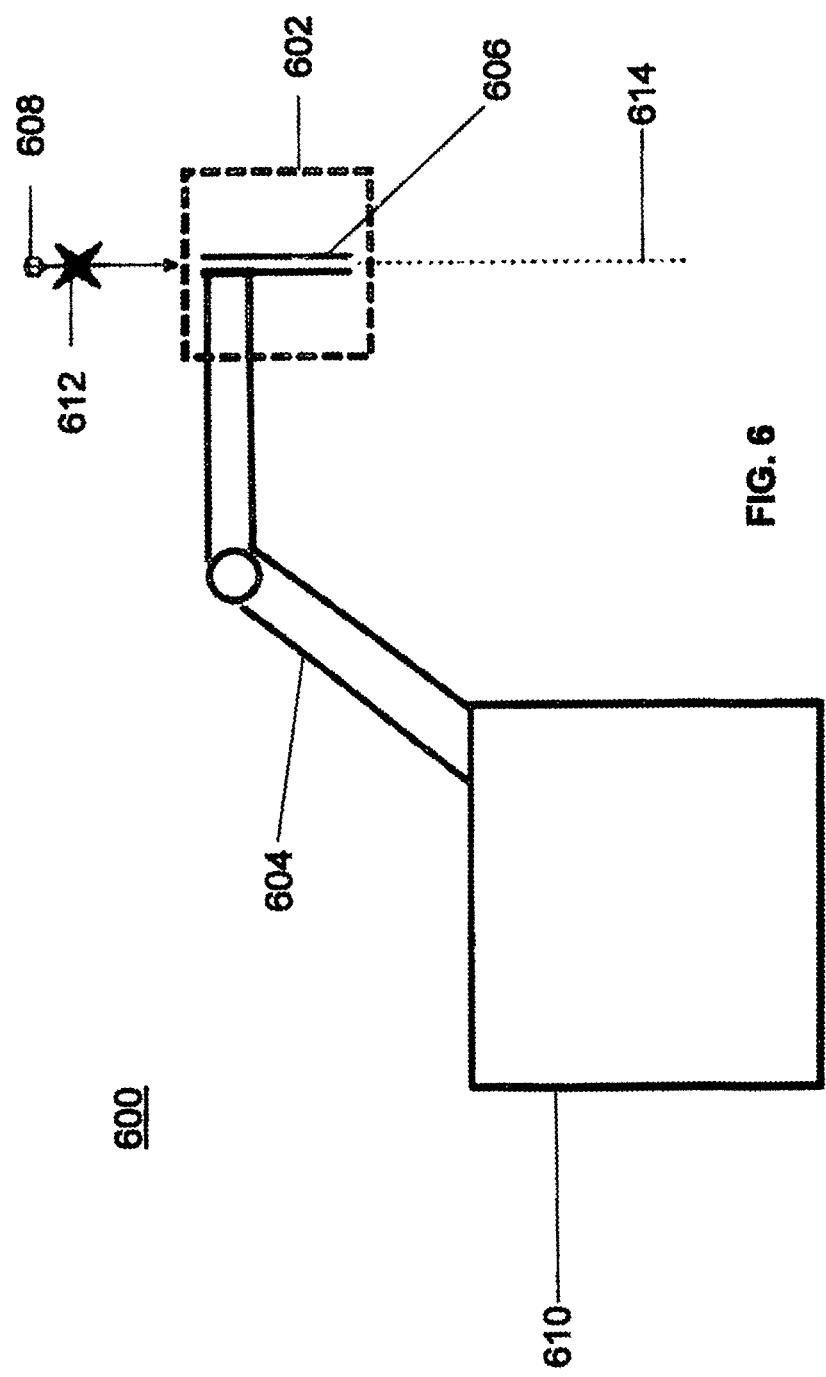
FIG. 6 illustrates a surgical robot in accordance with an exemplary embodiment.

FIG. 6 illustrates a surgical robot system 600 consistent with an exemplary embodiment. Surgical robot system 600 may comprise end-effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end-effector 602 so that surgical robot system 600 may assist a user (for example, a surgeon) in operating on the patient 210. Surgical robot system 600 may be consistent with previously described surgical robot system 100 and 300.

Figure 8:
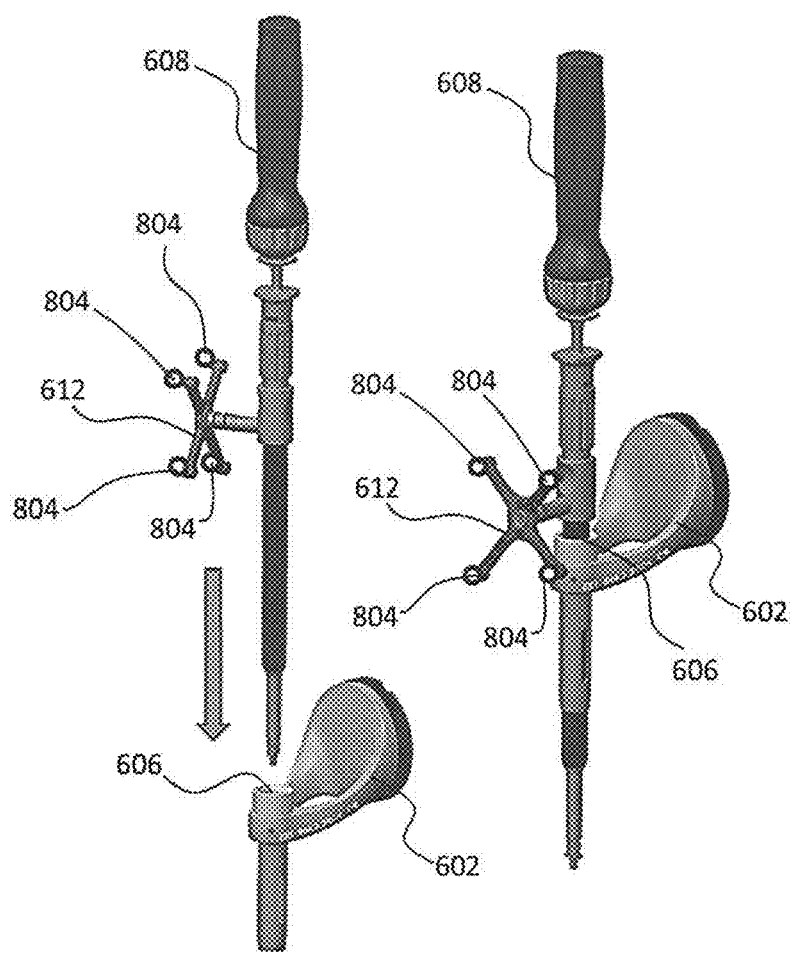
FIG. 8 illustrates a surgical instrument and the end-effector, before and after, inserting the surgical instrument into the guide tube of the end-effector according to one embodiment.

A tracking array 612 may be mounted on instrument 608 to monitor the location and orientation of instrument tool 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end-effector 602, and/or the patient 210. The tracking devices may be consistent with those structures described in connection with camera stand 302 and tracking subsystem 532.

FIGS. 7A, 7B, and 7C illustrate a top view, front view, and side view, respectively, of end-effector 602 consistent with an exemplary embodiment. End-effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end-effector 602 may be controlled by the system 100, 300, 600, and when the markers 702 are deactivated, the end-effector 602 may be locked in position and unable to be moved by the system 100, 300, 600.

Markers 702 may be disposed on or within end-effector 602 in a manner such that the markers 702 are visible by one or more cameras 200, 326 or other tracking devices associated with the surgical robot system 100, 300, 600. The camera 200, 326 or other tracking devices may track end-effector 602 as it moves to different positions and viewing angles by following the movement of tracking markers 702. The location of markers 702 and/or end-effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end-effector 602 is in a desirable position in relation to robot arm 604, robot base 610, the patient 210, and/or the user.

For example, as shown in FIG. 7A, markers 702 may be placed around the surface of end-effector 602 so that a tracking device placed away from the surgical field 208 and facing toward the robot 102, 301 and the camera 200, 326 is able to view at least 3 of the markers 702 through a range of common orientations of the end-effector 602 relative to the tracking device. For example, distribution of markers 702 in this way allows end-effector 602 to be monitored by the tracking devices when end-effector 602 is translated and rotated in the surgical field 208.

In addition, in exemplary embodiments, end-effector 602 may be equipped with infrared (IR) receivers that can detect when an external camera 200, 326 is getting ready to read markers 702. Upon this detection, end-effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end-effector 602 and adjust the instrument 608 is evident in FIG. 8. The hollow tube or guide tube 114, 606 of the end-effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screw driver is exemplified as the surgical tool 608, it will be appreciated that any suitable surgical tool 608 may be positioned by the end-effector 602. By way of example, the surgical instrument 608 may include one or more of a guide wire, cannula, a retractor, a drill, a reamer, a screw driver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

Figure 9:
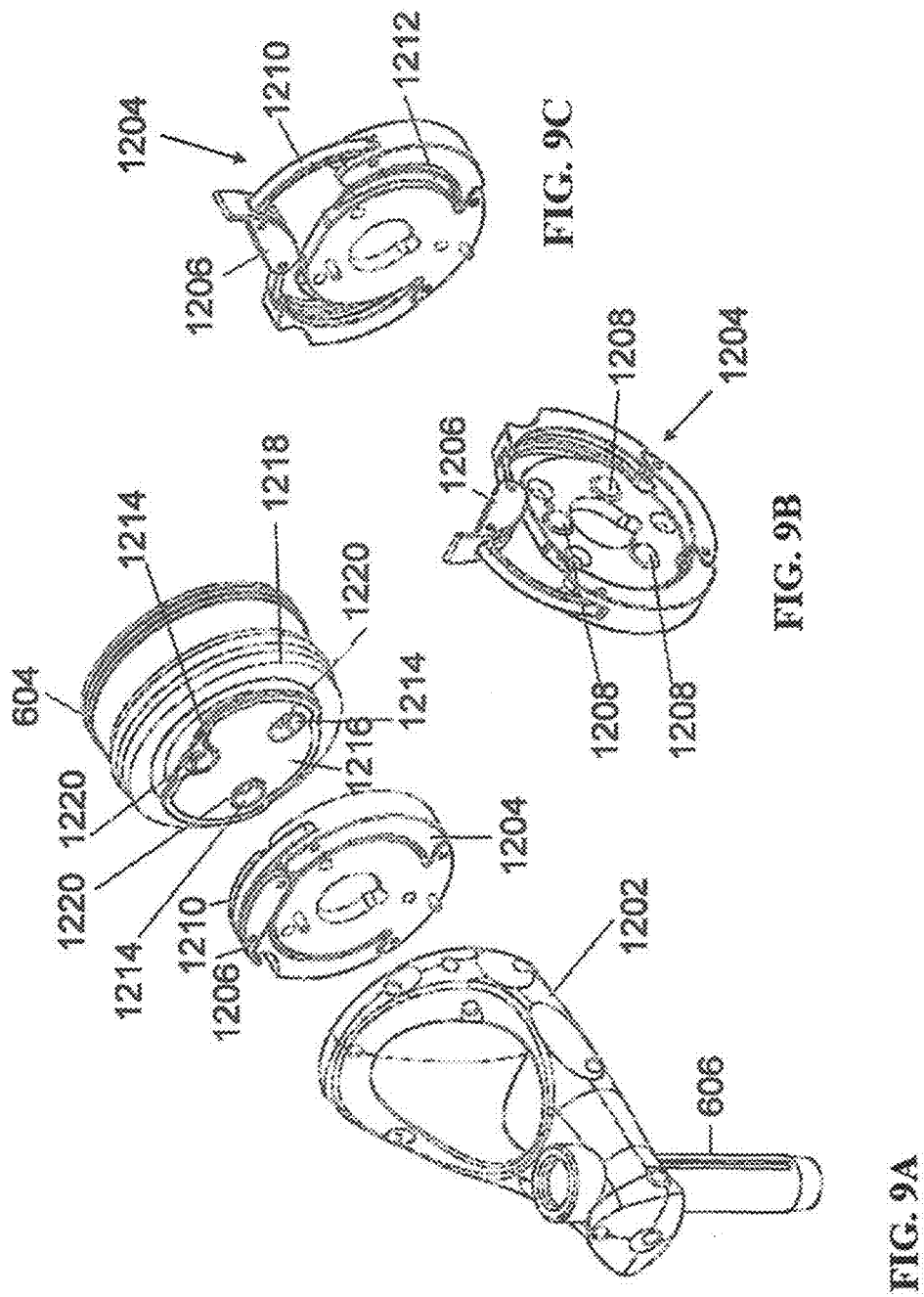
FIGS. 9A-9C illustrate portions of an end-effector and robot arm in accordance with an exemplary embodiment.

FIGS. 9A-9C illustrate end-effector 602 and a portion of robot arm 604 consistent with an exemplary embodiment. End-effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220.

End-effector 602 may mechanically interface and/or engage with the surgical robot system and robot arm 604 through one or more couplings. For example, end-effector 602 may engage with robot arm 604 through a locating coupling and/or a reinforcing coupling. Through these couplings, end-effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end-effector 602 regardless of the orientation of end-effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end-effector 602 to robot arm 604 as lip 1212 and lip 1218 engage clamp 1204 in a manner to secure end-effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end-effector 602 may be robustly secured to robot arm 604.

Spring 1210 may be a curved beam in tension. Spring 1210 may be comprised of a material that exhibits high stiffness and high yield strain such as virgin PEEK (polyether-ether-ketone). The linkage between end-effector 602 and robot arm 604 may provide for a sterile barrier between end-effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end-effector 602 and/or robot arm 604 that slips over an interface between end-effector 602 and robot arm 604 and tightens with a screw mechanism, an over center linkage, or a cam mechanism.

Figure 10:
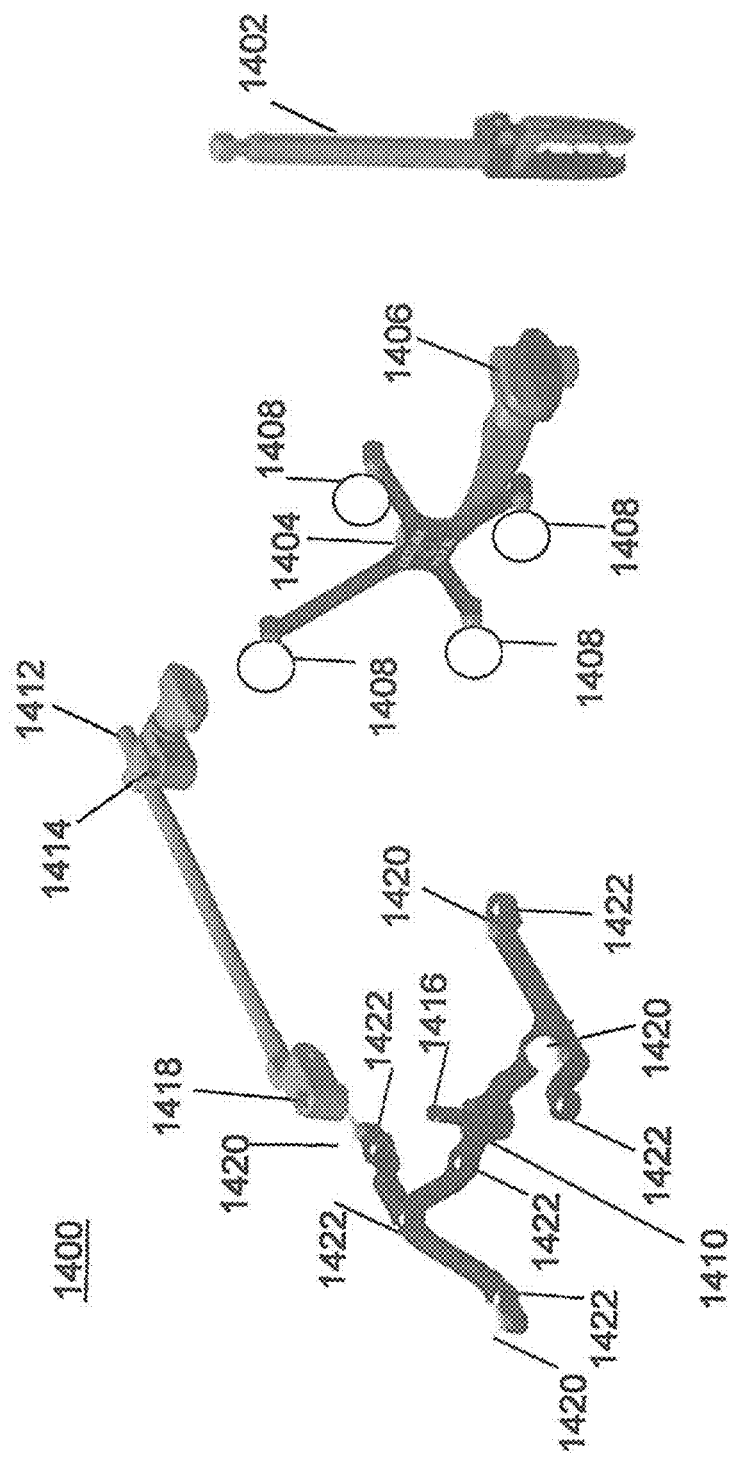
FIG. 10 illustrates a dynamic reference array, an imaging array, and other components in accordance with an exemplary embodiment.
Figure 11:
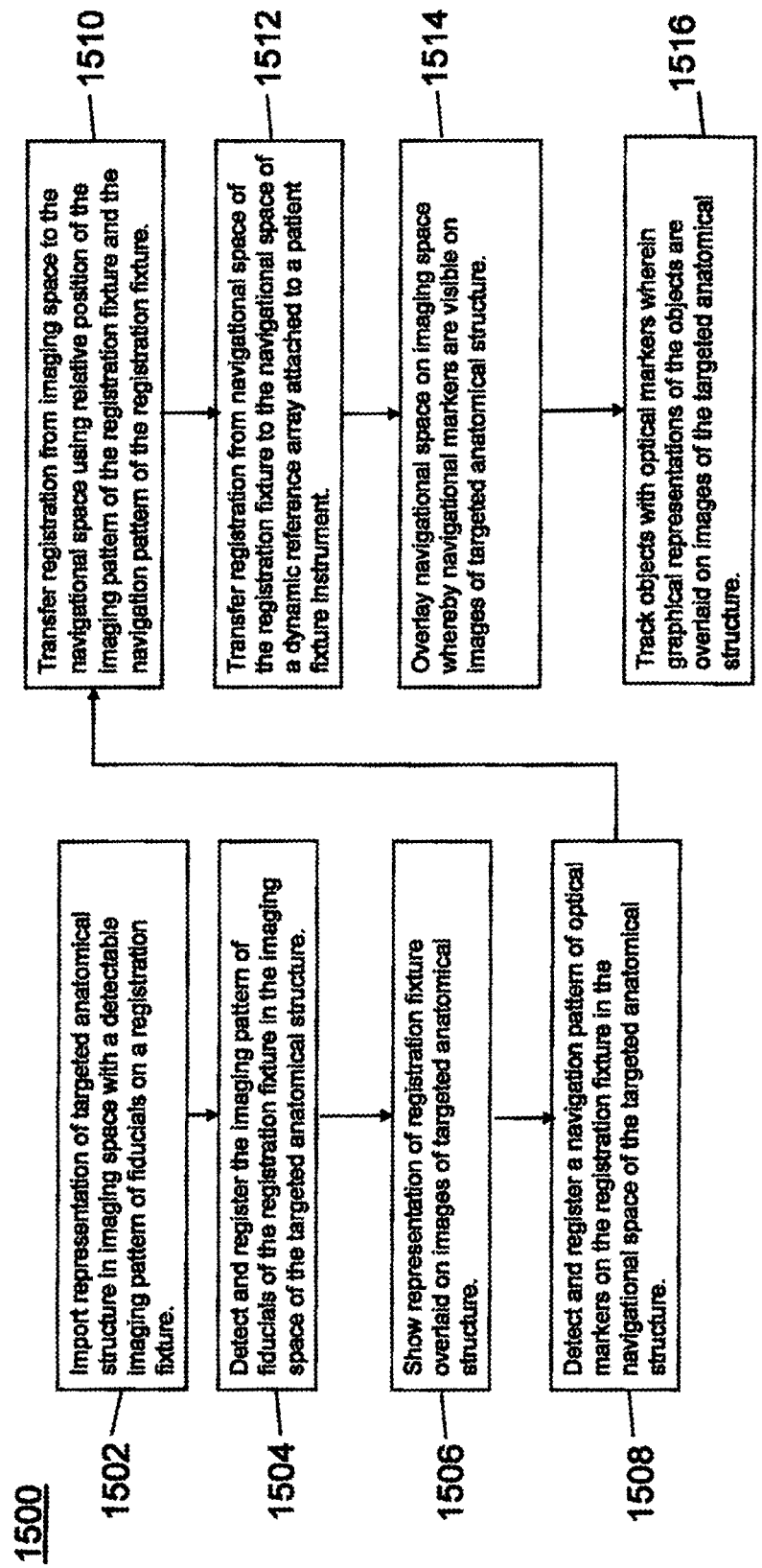
FIG. 11 illustrates a method of registration in accordance with an exemplary embodiment.

Referring to FIGS. 10 and 11, prior to or during a surgical procedure, certain registration procedures may be conducted to track objects and a target anatomical structure of the patient 210 both in a navigation space and an image space. To conduct such registration, a registration system 1400 may be used as illustrated in FIG. 10.

To track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 11 provides an exemplary method 1500 for registration consistent with the present disclosure. Method 1500 begins at step 1502 wherein a graphical representation (or image(s)) of the targeted anatomical structure may be imported into system 100, 300 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

Figure 12A:
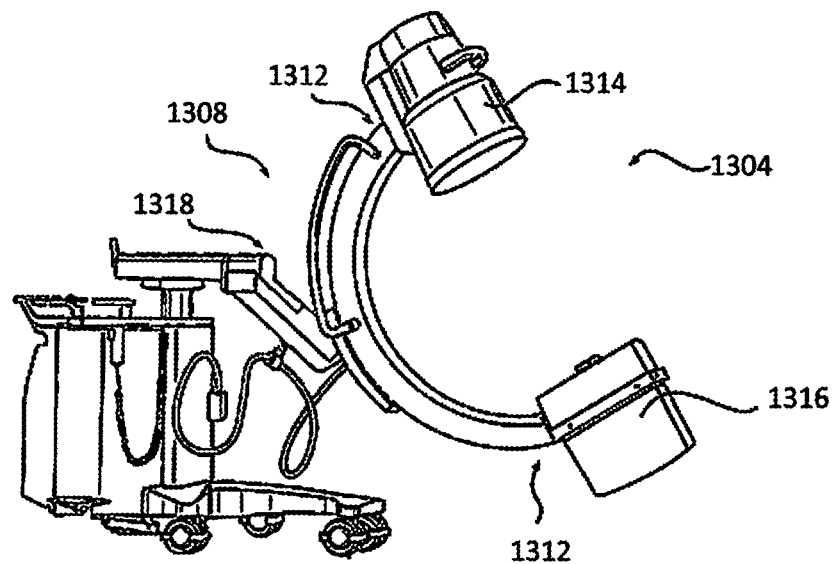
FIG. 12A-12B illustrate embodiments of imaging devices according to exemplary embodiments.
Figure 12B:
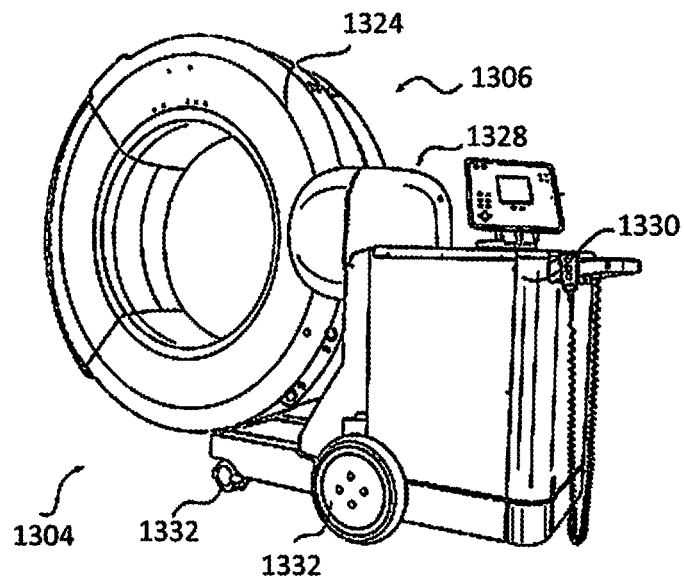

FIGS. 12A-12B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Turning now to FIGS. 13A-13C, the surgical robot system 100, 300, 600 relies on accurate positioning of the end-effector 112, 602, surgical instruments 608, and/or the patient 210 (e.g., patient tracking device 116) relative to the desired surgical area. In the embodiments shown in FIGS. 13A-13C, the tracking markers 118, 804 are rigidly attached to a portion of the instrument 608 and/or end-effector 112.

FIG. 13A depicts part of the surgical robot system 100 with the robot 102 including base 106, robot arm 104, and end-effector 112. The other elements, not illustrated, such as the display, cameras, etc. may also be present as described herein. FIG. 13B depicts a close-up view of the end-effector 112 with guide tube 114 and a plurality of tracking markers 118 rigidly affixed to the end-effector 112. In this embodiment, the plurality of tracking markers 118 are attached to the guide tube 112. FIG. 13C depicts an instrument 608 (in this case, a probe 608A) with a plurality of tracking markers 804 rigidly affixed to the instrument 608. As described elsewhere herein, the instrument 608 could include any suitable surgical instrument, such as, but not limited to, guide wire, cannula, a retractor, a drill, a reamer, a screw driver, an insertion tool, a removal tool, or the like.

When tracking an instrument 608, end-effector 112, or other object to be tracked in 3D, an array of tracking markers 118, 804 may be rigidly attached to a portion of the tool 608 or end-effector 112. Preferably, the tracking markers 118, 804 are attached such that the markers 118, 804 are out of the way (e.g., not impeding the surgical operation, visibility, etc.). The markers 118, 804 may be affixed to the instrument 608, end-effector 112, or other object to be tracked, for example, with an array 612. Usually three or four markers 118, 804 are used with an array 612. The array 612 may include a linear section, a cross piece, and may be asymmetric such that the markers 118, 804 are at different relative positions and locations with respect to one another. For example, as shown in FIG. 13C, a probe 608A with a 4-marker tracking array 612 is shown, and FIG. 13B depicts the end-effector 112 with a different 4-marker tracking array 612.

In FIG. 13C, the tracking array 612 functions as the handle 620 of the probe 608A. Thus, the four markers 804 are attached to the handle 620 of the probe 608A, which is out of the way of the shaft 622 and tip 624. Stereophotogrammetric tracking of these four markers 804 allows the instrument 608 to be tracked as a rigid body and for the tracking system 100, 300, 600 to precisely determine the position of the tip 624 and the orientation of the shaft 622 while the probe 608A is moved around in front of tracking cameras 200, 326.

To enable automatic tracking of one or more tools 608, end-effector 112, or other object to be tracked in 3D (e.g., multiple rigid bodies), the markers 118, 804 on each tool 608, end-effector 112, or the like, are arranged asymmetrically with a known inter-marker spacing. The reason for asymmetric alignment is so that it is unambiguous which marker 118, 804 corresponds to a particular location on the rigid body and whether markers 118, 804 are being viewed from the front or back, i.e., mirrored. For example, if the markers 118, 804 were arranged in a square on the tool 608 or end-effector 112, it would be unclear to the system 100, 300, 600 which marker 118, 804 corresponded to which corner of the square. For example, for the probe 608A, it would be unclear which marker 804 was closest to the shaft 622. Thus, it would be unknown which way the shaft 622 was extending from the array 612. Accordingly, each array 612 and thus each tool 608, end-effector 112, or other object to be tracked should have a unique marker pattern to allow it to be distinguished from other tools 608 or other objects being tracked. Asymmetry and unique marker patterns allow the system 100, 300, 600 to detect individual markers 118, 804 then to check the marker spacing against a stored template to determine which tool 608, end effector 112, or other object they represent. Detected markers 118, 804 can then be sorted automatically and assigned to each tracked object in the correct order. Without this information, rigid body calculations could not then be performed to extract key geometric information, for example, such as tool tip 624 and alignment of the shaft 622, unless the user manually specified which detected marker 118, 804 corresponded to which position on each rigid body. These concepts are commonly known to those skilled in the methods of 3D optical tracking.

Turning now to FIGS. 14A-14D, an alternative version of an end-effector 912 with moveable tracking markers 918A-918D is shown. In FIG. 14A, an array with moveable tracking markers 918A-918D are shown in a first configuration, and in FIG. 14B the moveable tracking markers 918A-918D are shown in a second configuration, which is angled relative to the first configuration. FIG. 14C shows the template of the tracking markers 918A-918D, for example, as seen by the cameras 200, 326 in the first configuration of FIG. 14A; and FIG. 14D shows the template of tracking markers 918A-918D, for example, as seen by the cameras 200, 326 in the second configuration of FIG. 14B.

In this embodiment, 4-marker array tracking is contemplated wherein the markers 918A-918D are not all in fixed position relative to the rigid body and instead, one or more of the array markers 918A-918D can be adjusted, for example, during testing, to give updated information about the rigid body that is being tracked without disrupting the process for automatic detection and sorting of the tracked markers 918A-918D.

When tracking any tool, such as a guide tube 914 connected to the end effector 912 of a robot system 100, 300, 600, the tracking array's primary purpose is to update the position of the end effector 912 in the camera coordinate system. When using the rigid system, for example, as shown in FIG. 13B, the array 612 of reflective markers 118 rigidly extend from the guide tube 114. Because the tracking markers 118 are rigidly connected, knowledge of the marker locations in the camera coordinate system also provides exact location of the centerline, tip, and tail of the guide tube 114 in the camera coordinate system. Typically, information about the position of the end effector 112 from such an array 612 and information about the location of a target trajectory from another tracked source are used to calculate the required moves that must be input for each axis of the robot 102 that will move the guide tube 114 into alignment with the trajectory and move the tip to a particular location along the trajectory vector.

Sometimes, the desired trajectory is in an awkward or unreachable location, but if the guide tube 114 could be swiveled, it could be reached. For example, a very steep trajectory pointing away from the base 106 of the robot 102 might be reachable if the guide tube 114 could be swiveled upward beyond the limit of the pitch (wrist up-down angle) axis, but might not be reachable if the guide tube 114 is attached parallel to the plate connecting it to the end of the wrist. To reach such a trajectory, the base 106 of the robot 102 might be moved or a different end effector 112 with a different guide tube attachment might be exchanged with the working end effector. Both of these solutions may be time consuming and cumbersome.

As best seen in FIGS. 14A and 14B, if the array 908 is configured such that one or more of the markers 918A-918D are not in a fixed position and instead, one or more of the markers 918A-918D can be adjusted, swiveled, pivoted, or moved, the robot 102 can provide updated information about the object being tracked without disrupting the detection and tracking process. For example, one of the markers 918A-918D may be fixed in position and the other markers 918A-918D may be moveable; two of the markers 918A-918D may be fixed in position and the other markers 918A-918D may be moveable; three of the markers 918A-918D may be fixed in position and the other marker 918A-918D may be moveable; or all of the markers 918A-918D may be moveable.

In the embodiment shown in FIGS. 14A and 14B, markers 918A, 918 B are rigidly connected directly to a base 906 of the end-effector 912, and markers 918C, 918D are rigidly connected to the tube 914. Similar to array 612, array 908 may be provided to attach the markers 918A-918D to the end-effector 912, instrument 608, or other object to be tracked. In this case, however, the array 908 is comprised of a plurality of separate components. For example, markers 918A, 918B may be connected to the base 906 with a first array 908A, and markers 918C, 918D may be connected to the guide tube 914 with a second array 908B. Marker 918A may be affixed to a first end of the first array 908A and marker 918B may be separated a linear distance and affixed to a second end of the first array 908A. While first array 908 is substantially linear, second array 908B has a bent or V-shaped configuration, with respective root ends, connected to the guide tube 914, and diverging therefrom to distal ends in a V-shape with marker 918C at one distal end and marker 918D at the other distal end. Although specific configurations are exemplified herein, it will be appreciated that other asymmetric designs including different numbers and types of arrays 908A, 908B and different arrangements, numbers, and types of markers 918A-918D are contemplated.

The guide tube 914 may be moveable, swivelable, or pivotable relative to the base 906, for example, across a hinge 920 or other connector to the base 906. Thus, markers 918C, 918D are moveable such that when the guide tube 914 pivots, swivels, or moves, markers 918C, 918D also pivot, swivel, or move. As best seen in FIG. 14A, guide tube 914 has a longitudinal axis 916 which is aligned in a substantially normal or vertical orientation such that markers 918A-918D have a first configuration. Turning now to FIG. 14B, the guide tube 914 is pivoted, swiveled, or moved such that the longitudinal axis 916 is now angled relative to the vertical orientation such that markers 918A-918D have a second configuration, different from the first configuration.

In contrast to the embodiment described for FIGS. 14A-14D, if a swivel existed between the guide tube 914 and the arm 104 (e.g., the wrist attachment) with all four markers 918A-918D remaining attached rigidly to the guide tube 914 and this swivel was adjusted by the user, the robotic system 100, 300, 600 would not be able to automatically detect that the guide tube 914 orientation had changed. The robotic system 100, 300, 600 would track the positions of the marker array 908 and would calculate incorrect robot axis moves assuming the guide tube 914 was attached to the wrist (the robot arm 104) in the previous orientation. By keeping one or more markers 918A-918D (e.g., two markers 918C, 918D) rigidly on the tube 914 and one or more markers 918A-918D (e.g., two markers 918A, 918B) across the swivel, automatic detection of the new position becomes possible and correct robot moves are calculated based on the detection of a new tool or end-effector 112, 912 on the end of the robot arm 104.

One or more of the markers 918A-918D are configured to be moved, pivoted, swiveled, or the like according to any suitable means. For example, the markers 918A-918D may be moved by a hinge 920, such as a clamp, spring, lever, slide, toggle, or the like, or any other suitable mechanism for moving the markers 918A-918D individually or in combination, moving the arrays 908A, 908B individually or in combination, moving any portion of the end-effector 912 relative to another portion, or moving any portion of the tool 608 relative to another portion.

As shown in FIGS. 14A and 14B, the array 908 and guide tube 914 may become reconfigurable by simply loosening the clamp or hinge 920, moving part of the array 908A, 908B relative to the other part 908A, 908B, and retightening the hinge 920 such that the guide tube 914 is oriented in a different position. For example, two markers 918C, 918D may be rigidly interconnected with the tube 914 and two markers 918A, 918B may be rigidly interconnected across the hinge 920 to the base 906 of the end-effector 912 that attaches to the robot arm 104. The hinge 920 may be in the form of a clamp, such as a wing nut or the like, which can be loosened and retightened to allow the user to quickly switch between the first configuration (FIG. 14A) and the second configuration (FIG. 14B).

The cameras 200, 326 detect the markers 918A-918D, for example, in one of the templates identified in FIGS. 14C and 14D. If the array 908 is in the first configuration (FIG. 14A) and tracking cameras 200, 326 detect the markers 918A-918D, then the tracked markers match Array Template 1 as shown in FIG. 14C. If the array 908 is the second configuration (FIG. 14B) and tracking cameras 200, 326 detect the same markers 918A-918D, then the tracked markers match Array Template 2 as shown in FIG. 14D. Array Template 1 and Array Template 2 are recognized by the system 100, 300, 600 as two distinct tools, each with its own uniquely defined spatial relationship between guide tube 914, markers 918A-918D, and robot attachment. The user could therefore adjust the position of the end-effector 912 between the first and second configurations without notifying the system 100, 300, 600 of the change and the system 100, 300, 600 would appropriately adjust the movements of the robot 102 to stay on trajectory.

In this embodiment, there are two assembly positions in which the marker array matches unique templates that allow the system 100, 300, 600 to recognize the assembly as two different tools or two different end effectors. In any position of the swivel between or outside of these two positions (namely, Array Template 1 and Array Template 2 shown in FIGS. 14C and 14D, respectively), the markers 918A-918D would not match any template and the system 100, 300, 600 would not detect any array present despite individual markers 918A-918D being detected by cameras 200, 326, with the result being the same as if the markers 918A-918D were temporarily blocked from view of the cameras 200, 326. It will be appreciated that other array templates may exist for other configurations, for example, identifying different instruments 608 or other end-effectors 112, 912, etc.

In the embodiment described, two discrete assembly positions are shown in FIGS. 14A and 14B. It will be appreciated, however, that there could be multiple discrete positions on a swivel joint, linear joint, combination of swivel and linear joints, pegboard, or other assembly where unique marker templates may be created by adjusting the position of one or more markers 918A-918D of the array relative to the others, with each discrete position matching a particular template and defining a unique tool 608 or end-effector 112, 912 with different known attributes. In addition, although exemplified for end effector 912, it will be appreciated that moveable and fixed markers 918A-918D may be used with any suitable instrument 608 or other object to be tracked.

When using an external 3D tracking system 100, 300, 600 to track a full rigid body array of three or more markers attached to a robot's end effector 112 (for example, as depicted in FIGS. 13A and 13B), it is possible to directly track or to calculate the 3D position of every section of the robot 102 in the coordinate system of the cameras 200, 326. The geometric orientations of joints relative to the tracker are known by design, and the linear or angular positions of joints are known from encoders for each motor of the robot 102, fully defining the 3D positions of all of the moving parts from the end effector 112 to the base 116. Similarly, if a tracker were mounted on the base 106 of the robot 102 (not shown), it is likewise possible to track or calculate the 3D position of every section of the robot 102 from base 106 to end effector 112 based on known joint geometry and joint positions from each motor's encoder.

In some situations, it may be desirable to track the positions of all segments of the robot 102 from fewer than three markers 118 rigidly attached to the end effector 112. Specifically, if a tool 608 is introduced into the guide tube 114, it may be desirable to track full rigid body motion of the robot 902 with only one additional marker 118 being tracked.

Turning now to FIGS. 15A-15E, an alternative version of an end-effector 1012 having only a single tracking marker 1018 is shown. End-effector 1012 may be similar to the other end-effectors described herein, and may include a guide tube 1014 extending along a longitudinal axis 1016. A single tracking marker 1018, similar to the other tracking markers described herein, may be rigidly affixed to the guide tube 1014. This single marker 1018 can serve the purpose of adding missing degrees of freedom to allow full rigid body tracking and/or can serve the purpose of acting as a surveillance marker to ensure that assumptions about robot and camera positioning are valid.

The single tracking marker 1018 may be attached to the robotic end effector 1012 as a rigid extension to the end effector 1012 that protrudes in any convenient direction and does not obstruct the surgeon's view. The tracking marker 1018 may be affixed to the guide tube 1014 or any other suitable location of on the end-effector 1012. When affixed to the guide tube 1014, the tracking marker 1018 may be positioned at a location between first and second ends of the guide tube 1014. For example, in FIG. 15A, the single tracking marker 1018 is shown as a reflective sphere mounted on the end of a narrow shaft 1017 that extends forward from the guide tube 1014 and is positioned longitudinally above a mid-point of the guide tube 1014 and below the entry of the guide tube 1014. This position allows the marker 1018 to be generally visible by cameras 200, 326 but also would not obstruct vision of the surgeon 120 or collide with other tools or objects in the vicinity of surgery. In addition, the guide tube 1014 with the marker 1018 in this position is designed for the marker array on any tool 608 introduced into the guide tube 1014 to be visible at the same time as the single marker 1018 on the guide tube 1014 is visible.

Figure 15A:
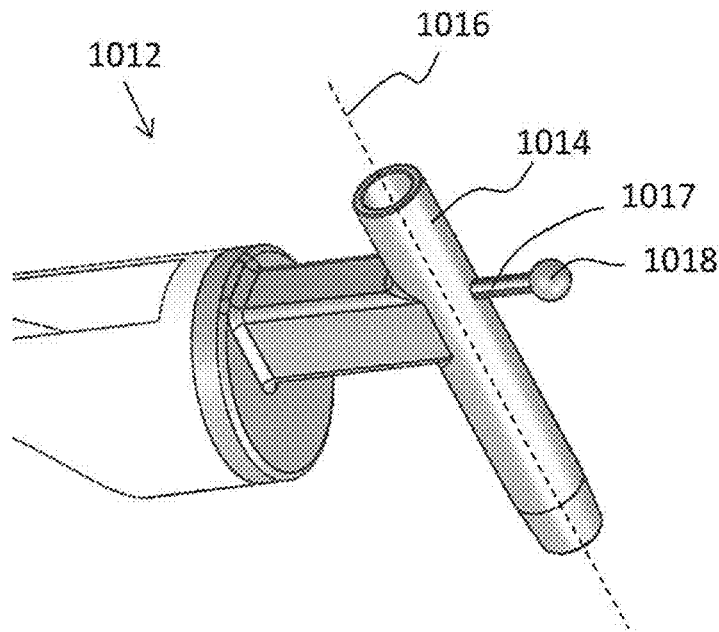
FIG. 15A shows an alternative version of the end-effector having only a single tracking marker affixed thereto.
Figure 15B:
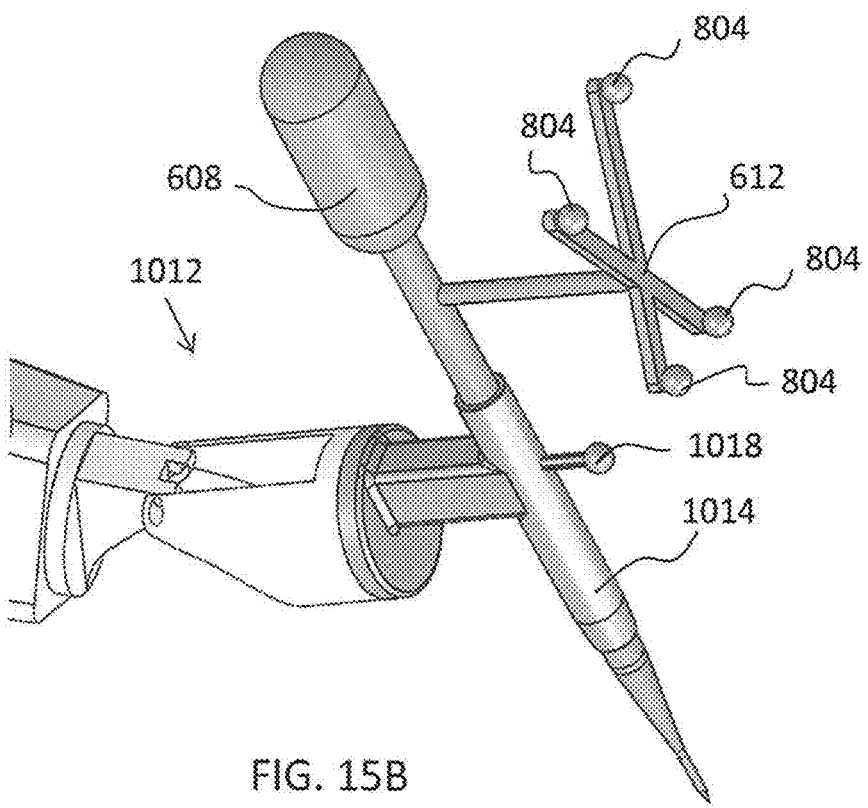
FIG. 15B shows the end-effector of FIG. 15A with an instrument disposed through the guide tube.

As shown in FIG. 15B, when a snugly fitting tool or instrument 608 is placed within the guide tube 1014, the instrument 608 becomes mechanically constrained in 4 of 6 degrees of freedom. That is, the instrument 608 cannot be rotated in any direction except about the longitudinal axis 1016 of the guide tube 1014 and the instrument 608 cannot be translated in any direction except along the longitudinal axis 1016 of the guide tube 1014. In other words, the instrument 608 can only be translated along and rotated about the centerline of the guide tube 1014. If two more parameters are known, such as (1) an angle of rotation about the longitudinal axis 1016 of the guide tube 1014; and (2) a position along the guide tube 1014, then the position of the end effector 1012 in the camera coordinate system becomes fully defined.

Figure 15C:
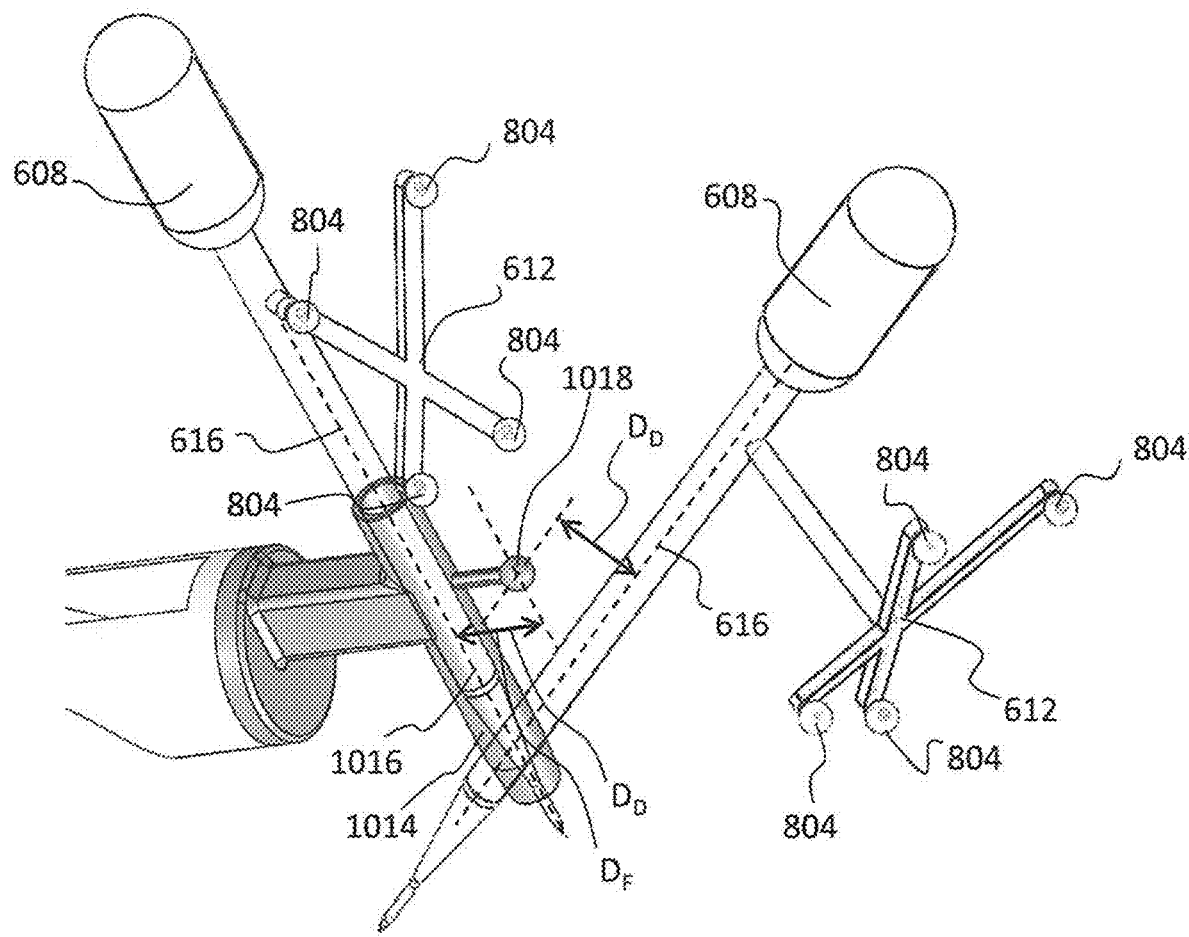
FIG. 15C shows the end-effector of FIG. 15A with the instrument in two different positions, and the resulting logic to determine if the instrument is positioned within the guide tube or outside of the guide tube.

Referring now to FIG. 15C, the system 100, 300, 600 should be able to know when a tool 608 is actually positioned inside of the guide tube 1014 and is not instead outside of the guide tube 1014 and just somewhere in view of the cameras 200, 326. The tool 608 has a longitudinal axis or centerline 616 and an array 612 with a plurality of tracked markers 804. The rigid body calculations may be used to determine where the centerline 616 of the tool 608 is located in the camera coordinate system based on the tracked position of the array 612 on the tool 608.

The fixed normal (perpendicular) distance $D_F$ from the single marker 1018 to the centerline or longitudinal axis 1016 of the guide tube 1014 is fixed and is known geometrically, and the position of the single marker 1018 can be tracked. Therefore, when a detected distance $D_D$ from tool centerline 616 to single marker 1018 matches the known fixed distance $D_F$ from the guide tube centerline 1016 to the single marker 1018, it can be determined that the tool 608 is either within the guide tube 1014 (centerlines 616, 1016 of tool 608 and guide tube 1014 coincident) or happens to be at some point in the locus of possible positions where this distance $D_D$ matches the fixed distance $D_F$. For example, in FIG. 15C, the normal detected distance $D_D$ from tool centerline 616 to the single marker 1018 matches the fixed distance $D_F$ from guide tube centerline 1016 to the single marker 1018 in both frames of data (tracked marker coordinates) represented by the transparent tool 608 in two positions, and thus, additional considerations may be needed to determine when the tool 608 is located in the guide tube 1014.

Figure 15D:
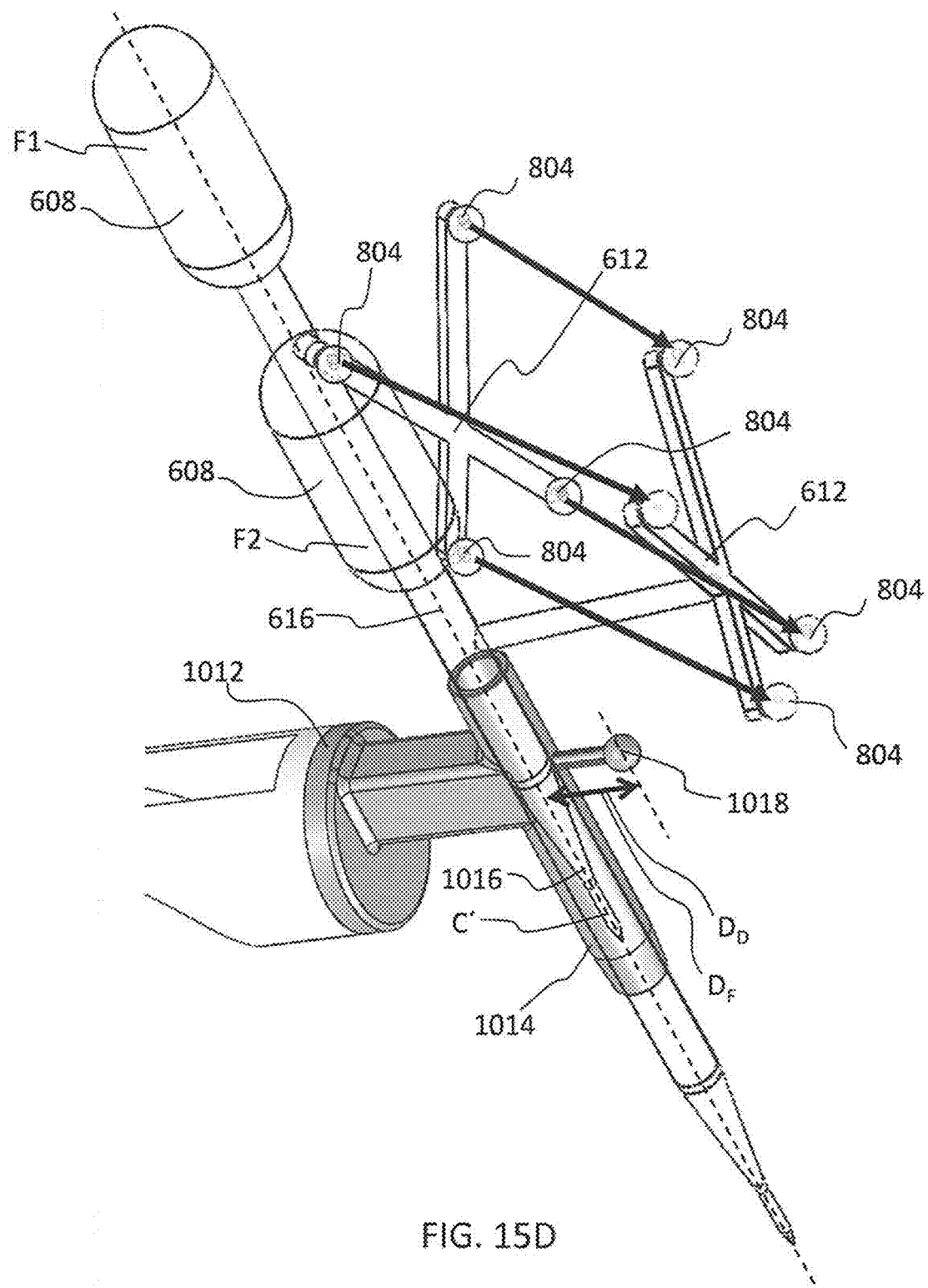
FIG. 15D shows the end-effector of FIG. 15A with the instrument in the guide tube at two different frames and its relative distance to the single tracking marker on the guide tube.

Turning now to FIG. 15D, programmed logic can be used to look for frames of tracking data in which the detected distance $D_D$ from tool centerline 616 to single marker 1018 remains fixed at the correct length despite the tool 608 moving in space by more than some minimum distance relative to the single sphere 1018 to satisfy the condition that the tool 608 is moving within the guide tube 1014. For example, a first frame F1 may be detected with the tool 608 in a first position and a second frame F2 may be detected with the tool 608 in a second position (namely, moved linearly with respect to the first position). The markers 804 on the tool array 612 may move by more than a given amount (e.g., more than 5 mm total) from the first frame F1 to the second frame F2. Even with this movement, the detected distance $D_D$ from the tool centerline vector C' to the single marker 1018 is substantially identical in both the first frame F1 and the second frame F2.

Logistically, the surgeon 120 or user could place the tool 608 within the guide tube 1014 and slightly rotate it or slide it down into the guide tube 1014 and the system 100, 300, 600 would be able to detect that the tool 608 is within the guide tube 1014 from tracking of the five markers (four markers 804 on tool 608 plus single marker 1018 on guide tube 1014). Knowing that the tool 608 is within the guide tube 1014, all 6 degrees of freedom may be calculated that define the position and orientation of the robotic end effector 1012 in space. Without the single marker 1018, even if it is known with certainty that the tool 608 is within the guide tube 1014, it is unknown where the guide tube 1014 is located along the tool's centerline vector C' and how the guide tube 1014 is rotated relative to the centerline vector C'.

Figure 15E:
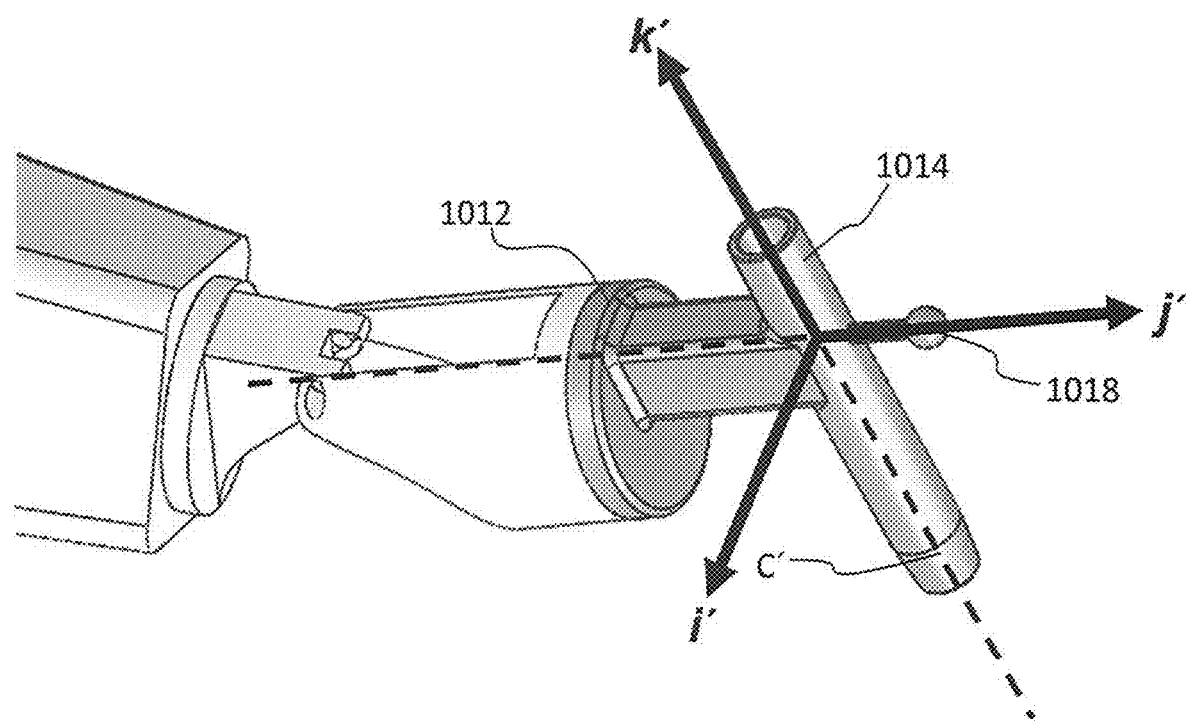
FIG. 15E shows the end-effector of FIG. 15A relative to a coordinate system.

With emphasis on FIG. 15E, the presence of the single marker 1018 being tracked as well as the four markers 804 on the tool 608, it is possible to construct the centerline vector C' of the guide tube 1014 and tool 608 and the normal vector through the single marker 1018 and through the centerline vector C'. This normal vector has an orientation that is in a known orientation relative to the forearm of the robot distal to the wrist (in this example, oriented parallel to that segment) and intersects the centerline vector C' at a specific fixed position. For convenience, three mutually orthogonal vectors k', j', i' can be constructed, as shown in FIG. 15E, defining rigid body position and orientation of the guide tube 1014. One of the three mutually orthogonal vectors k' is constructed from the centerline vector C', the second vector j' is constructed from the normal vector through the single marker 1018, and the third vector i' is the vector cross product of the first and second vectors k', j'. The robot's joint positions relative to these vectors k', j', i' are known and fixed when all joints are at zero, and therefore rigid body calculations can be used to determine the location of any section of the robot relative to these vectors k', j', i' when the robot is at a home position. During robot movement, if the positions of the tool markers 804 (while the tool 608 is in the guide tube 1014) and the position of the single marker 1018 are detected from the tracking system, and angles/linear positions of each joint are known from encoders, then position and orientation of any section of the robot can be determined.

In some embodiments, it may be useful to fix the orientation of the tool 608 relative to the guide tube 1014. For example, the end effector guide tube 1014 may be oriented in a particular position about its axis 1016 to allow machining or implant positioning. Although the orientation of anything attached to the tool 608 inserted into the guide tube 1014 is known from the tracked markers 804 on the tool 608, the rotational orientation of the guide tube 1014 itself in the camera coordinate system is unknown without the additional tracking marker 1018 (or multiple tracking markers in other embodiments) on the guide tube 1014. This marker 1018 provides essentially a "clock position" from −180° to +180° based on the orientation of the marker 1018 relative to the centerline vector C'. Thus, the single marker 1018 can provide additional degrees of freedom to allow full rigid body tracking and/or can act as a surveillance marker to ensure that assumptions about the robot and camera positioning are valid.

Figure 16:
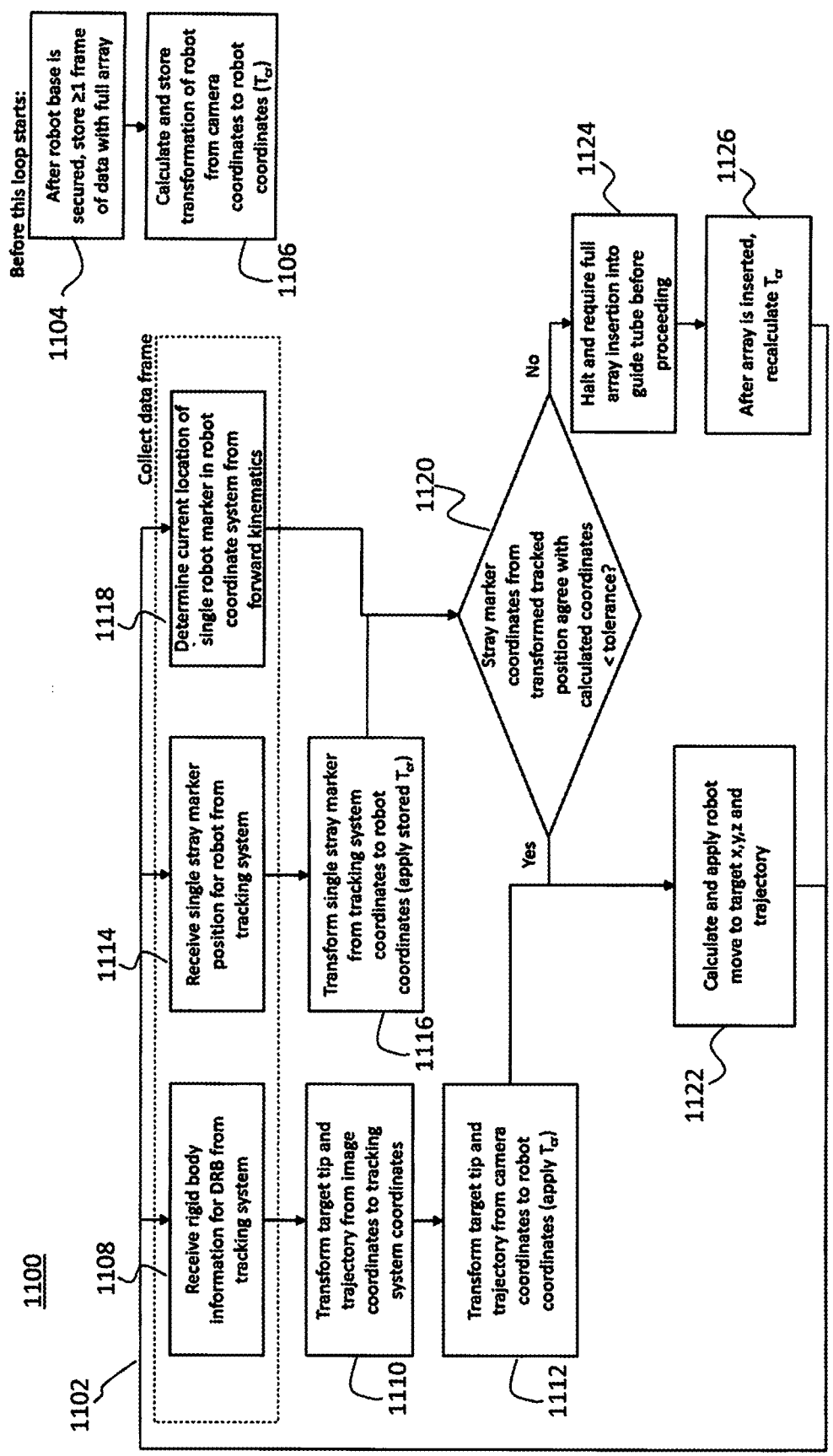
FIG. 16 is a block diagram of a method for navigating and moving the end-effector of the robot to a desired target trajectory.

FIG. 16 is a block diagram of a method 1100 for navigating and moving the end-effector 1012 (or any other end-effector described herein) of the robot 102 to a desired target trajectory. Another use of the single marker 1018 on the robotic end effector 1012 or guide tube 1014 is as part of the method 1100 enabling the automated safe movement of the robot 102 without a full tracking array attached to the robot 102. This method 1100 functions when the tracking cameras 200, 326 do not move relative to the robot 102 (i.e., they are in a fixed position), the tracking system's coordinate system and robot's coordinate system are co-registered, and the robot 102 is calibrated such that the position and orientation of the guide tube 1014 can be accurately determined in the robot's Cartesian coordinate system based only on the encoded positions of each robotic axis.

For this method 1100, the coordinate systems of the tracker and the robot must be co-registered, meaning that the coordinate transformation from the tracking system's Cartesian coordinate system to the robot's Cartesian coordinate system is needed. For convenience, this coordinate transformation can be a 4×4 matrix of translations and rotations that is well known in the field of robotics. This transformation will be termed Tcr to refer to "transformation—camera to robot". Once this transformation is known, any new frame of tracking data, which is received as x,y,z coordinates in vector form for each tracked marker, can be multiplied by the 4×4 matrix and the resulting x,y,z coordinates will be in the robot's coordinate system. To obtain Tcr, a full tracking array on the robot is tracked while it is rigidly attached to the robot at a location that is known in the robot's coordinate system, then known rigid body methods are used to calculate the transformation of coordinates. It should be evident that any tool 608 inserted into the guide tube 1014 of the robot 102 can provide the same rigid body information as a rigidly attached array when the additional marker 1018 is also read. That is, the tool 608 need only be inserted to any position within the guide tube 1014 and at any rotation within the guide tube 1014, not to a fixed position and orientation. Thus, it is possible to determine Tcr by inserting any tool 608 with a tracking array 612 into the guide tube 1014 and reading the tool's array 612 plus the single marker 1018 of the guide tube 1014 while at the same time determining from the encoders on each axis the current location of the guide tube 1014 in the robot's coordinate system.

Logic for navigating and moving the robot 102 to a target trajectory is provided in the method 1100 of FIG. 16. Before entering the loop 1102, it is assumed that the transformation Tcr was previously stored. Thus, before entering loop 1102, in step 1104, after the robot base 106 is secured, greater than or equal to one frame of tracking data of a tool inserted in the guide tube while the robot is static is stored; and in step 1106, the transformation of robot guide tube position from camera coordinates to robot coordinates Tcr is calculated from this static data and previous calibration data. Tcr should remain valid as long as the cameras 200, 326 do not move relative to the robot 102. If the cameras 200, 326 move relative to the robot 102, and Tcr needs to be re-obtained, the system 100, 300, 600 can be made to prompt the user to insert a tool 608 into the guide tube 1014 and then automatically perform the necessary calculations.

In the flowchart of method 1100, each frame of data collected consists of the tracked position of the DRB 1404 on the patient 210, the tracked position of the single marker 1018 on the end effector 1014, and a snapshot of the positions of each robotic axis. From the positions of the robot's axes, the location of the single marker 1018 on the end effector 1012 is calculated. This calculated position is compared to the actual position of the marker 1018 as recorded from the tracking system. If the values agree, it can be assured that the robot 102 is in a known location. The transformation Tcr is applied to the tracked position of the DRB 1404 so that the target for the robot 102 can be provided in terms of the robot's coordinate system. The robot 102 can then be commanded to move to reach the target.

After steps 1104, 1106, loop 1102 includes step 1108 receiving rigid body information for DRB 1404 from the tracking system; step 1110 transforming target tip and trajectory from image coordinates to tracking system coordinates; and step 1112 transforming target tip and trajectory from camera coordinates to robot coordinates (apply Tcr). Loop 1102 further includes step 1114 receiving a single stray marker position for robot from tracking system; and step 1116 transforming the single stray marker from tracking system coordinates to robot coordinates (apply stored Tcr). Loop 1102 also includes step 1118 determining current location of the single robot marker 1018 in the robot coordinate system from forward kinematics. The information from steps 1116 and 1118 is used to determine step 1120 whether the stray marker coordinates from transformed tracked position agree with the calculated coordinates being less than a given tolerance. If yes, proceed to step 1122, calculate and apply robot move to target x, y, z and trajectory. If no, proceed to step 1124, halt and require full array insertion into guide tube 1014 before proceeding; step 1126 after array is inserted, recalculate Tcr; and then proceed to repeat steps 1108, 1114, and 1118.

This method 1100 has advantages over a method in which the continuous monitoring of the single marker 1018 to verify the location is omitted. Without the single marker 1018, it would still be possible to determine the position of the end effector 1012 using Tcr and to send the end-effector 1012 to a target location but it would not be possible to verify that the robot 102 was actually in the expected location. For example, if the cameras 200, 326 had been bumped and Tcr was no longer valid, the robot 102 would move to an erroneous location. For this reason, the single marker 1018 provides value with regard to safety.

For a given fixed position of the robot 102, it is theoretically possible to move the tracking cameras 200, 326 to a new location in which the single tracked marker 1018 remains unmoved since it is a single point, not an array. In such a case, the system 100, 300, 600 would not detect any error since there would be agreement in the calculated and tracked locations of the single marker 1018. However, once the robot's axes caused the guide tube 1012 to move to a new location, the calculated and tracked positions would disagree and the safety check would be effective.

The term "surveillance marker" may be used, for example, in reference to a single marker that is in a fixed location relative to the DRB 1404. In this instance, if the DRB 1404 is bumped or otherwise dislodged, the relative location of the surveillance marker changes and the surgeon 120 can be alerted that there may be a problem with navigation. Similarly, in the embodiments described herein, with a single marker 1018 on the robot's guide tube 1014, the system 100, 300, 600 can continuously check whether the cameras 200, 326 have moved relative to the robot 102. If registration of the tracking system's coordinate system to the robot's coordinate system is lost, such as by cameras 200, 326 being bumped or malfunctioning or by the robot malfunctioning, the system 100, 300, 600 can alert the user and corrections can be made. Thus, this single marker 1018 can also be thought of as a surveillance marker for the robot 102.

It should be clear that with a full array permanently mounted on the robot 102 (e.g., the plurality of tracking markers 702 on end-effector 602 shown in FIGS. 7A-7C) such functionality of a single marker 1018 as a robot surveillance marker is not needed because it is not required that the cameras 200, 326 be in a fixed position relative to the robot 102, and Tcr is updated at each frame based on the tracked position of the robot 102. Reasons to use a single marker 1018 instead of a full array are that the full array is more bulky and obtrusive, thereby blocking the surgeon's view and access to the surgical field 208 more than a single marker 1018, and line of sight to a full array is more easily blocked than line of sight to a single marker 1018.

Turning now to FIGS. 17A-17B and 18A-18B, instruments 608, such as implant holders 608B, 608C, are depicted which include both fixed and moveable tracking markers 804, 806. The implant holders 608B, 608C may have a handle 620 and an outer shaft 622 extending from the handle 620. The shaft 622 may be positioned substantially perpendicular to the handle 620, as shown, or in any other suitable orientation. An inner shaft 626 may extend through the outer shaft 622 with a knob 628 at one end. Implant 10, 12 connects to the shaft 622, at the other end, at tip 624 of the implant holder 608B, 608C using typical connection mechanisms known to those of skill in the art. The knob 628 may be rotated, for example, to expand or articulate the implant 10, 12. U.S. Pat. Nos. 8,709,086 and 8,491,659, which are incorporated by reference herein, describe expandable fusion devices and methods of installation.

When tracking the tool 608, such as implant holder 608B, 608C, the tracking array 612 may contain a combination of fixed markers 804 and one or more moveable markers 806 which make up the array 612 or is otherwise attached to the implant holder 608B, 608C. The navigation array 612 may include at least one or more (e.g., at least two) fixed position markers 804, which are positioned with a known location relative to the implant holder instrument 608B, 608C. These fixed markers 804 would not be able to move in any orientation relative to the instrument geometry and would be useful in defining where the instrument 608 is in space. In addition, at least one marker 806 is present which can be attached to the array 612 or the instrument itself which is capable of moving within a pre-determined boundary (e.g., sliding, rotating, etc.) relative to the fixed markers 804. The system 100, 300, 600 (e.g., the software) correlates the position of the moveable marker 806 to a particular position, orientation, or other attribute of the implant 10 (such as height of an expandable interbody spacer shown in FIGS. 17A-17B or angle of an articulating interbody spacer shown in FIGS. 18A-18B). Thus, the system and/or the user can determine the height or angle of the implant 10, 12 based on the location of the moveable marker 806.

Figure 17A:
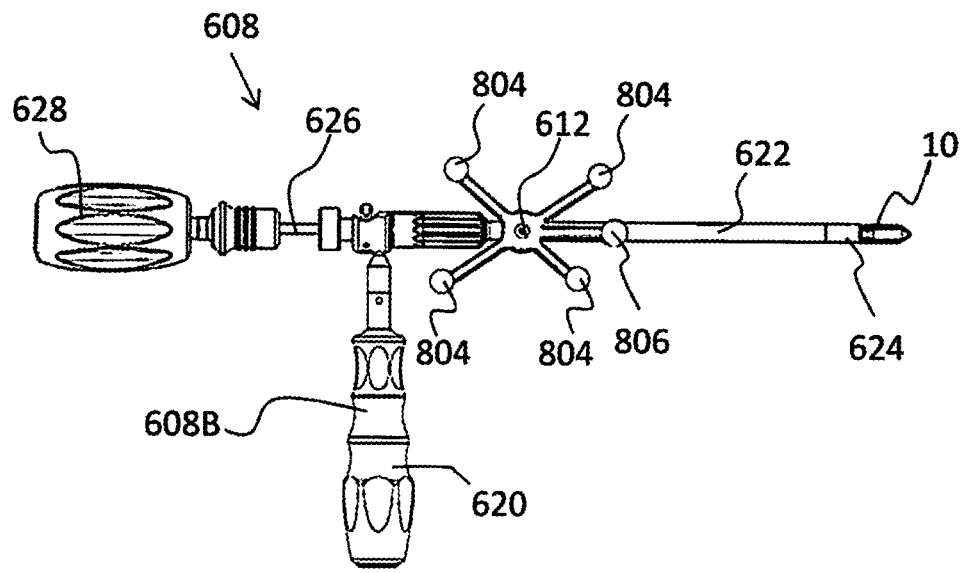
FIGS. 17A-17B depict an instrument for inserting an expandable implant having fixed and moveable tracking markers in contracted and expanded positions, respectively.
Figure 17B:
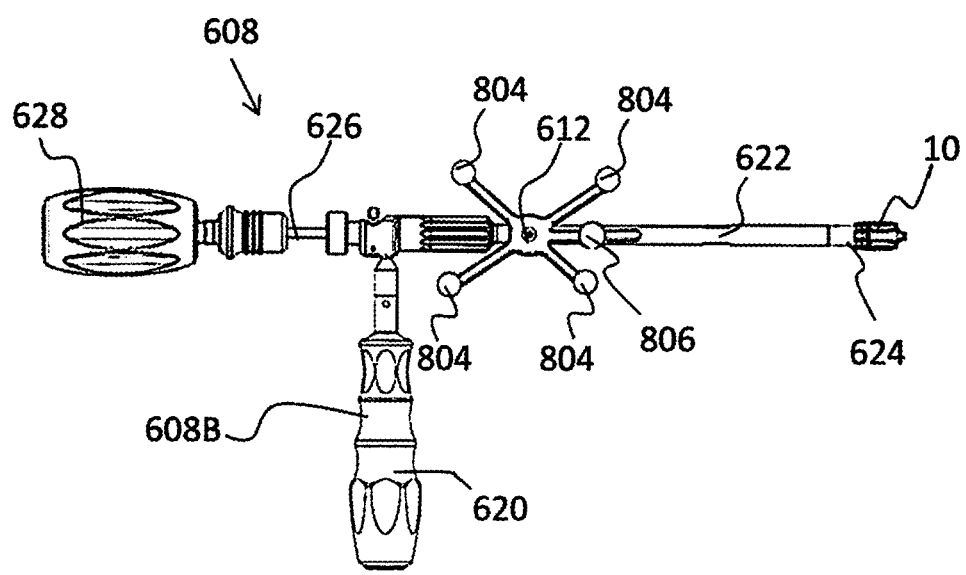

In the embodiment shown in FIGS. 17A-17B, four fixed markers 804 are used to define the implant holder 608B and a fifth moveable marker 806 is able to slide within a pre-determined path to provide feedback on the implant height (e.g., a contracted position or an expanded position). FIG. 17A shows the expandable spacer 10 at its initial height, and FIG. 17B shows the spacer 10 in the expanded state with the moveable marker 806 translated to a different position. In this case, the moveable marker 806 moves closer to the fixed markers 804 when the implant 10 is expanded, although it is contemplated that this movement may be reversed or otherwise different. The amount of linear translation of the marker 806 would correspond to the height of the implant 10. Although only two positions are shown, it would be possible to have this as a continuous function whereby any given expansion height could be correlated to a specific position of the moveable marker 806.

Figure 18A:
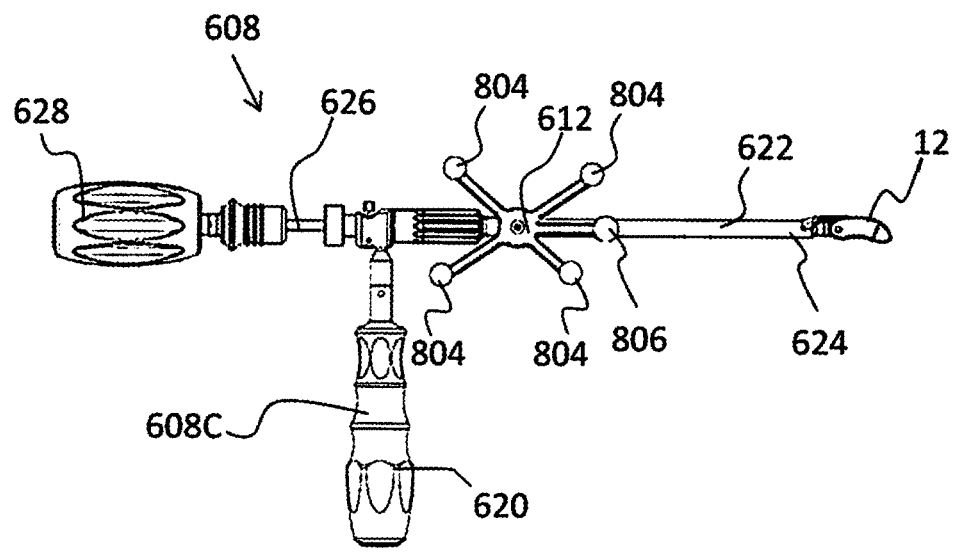
FIGS. 18A-18B depict an instrument for inserting an articulating implant having fixed and moveable tracking markers in insertion and angled positions, respectively.
Figure 18B:
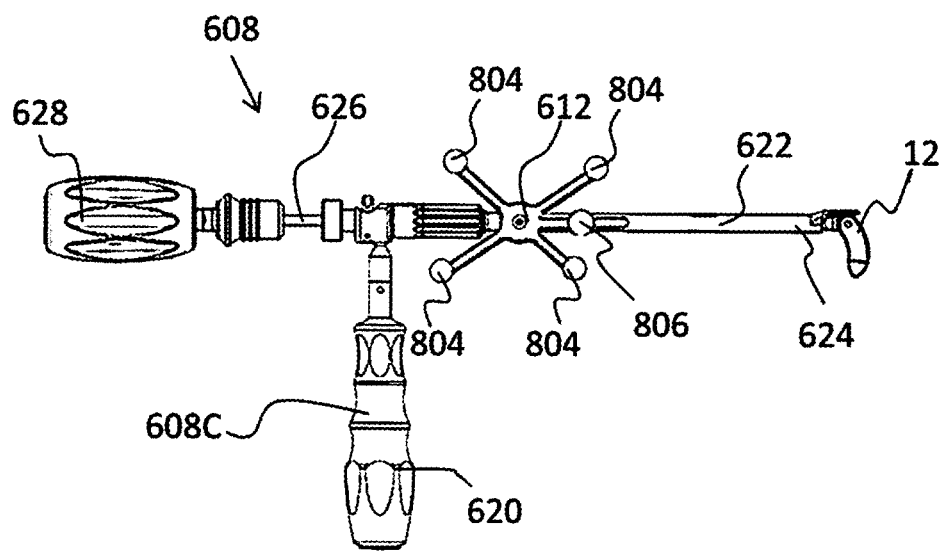

Turning now to FIGS. 18A-18B, four fixed markers 804 are used to define the implant holder 608C and a fifth, moveable marker 806 is configured to slide within a pre-determined path to provide feedback on the implant articulation angle. FIG. 18A shows the articulating spacer 12 at its initial linear state, and FIG. 18B shows the spacer 12 in an articulated state at some offset angle with the moveable marker 806 translated to a different position. The amount of linear translation of the marker 806 would correspond to the articulation angle of the implant 12. Although only two positions are shown, it would be possible to have this as a continuous function whereby any given articulation angle could be correlated to a specific position of the moveable marker 806.

In these embodiments, the moveable marker 806 slides continuously to provide feedback about an attribute of the implant 10, 12 based on position. It is also contemplated that there may be discreet positions that the moveable marker 806 must be in which would also be able to provide further information about an implant attribute. In this case, each discreet configuration of all markers 804, 806 correlates to a specific geometry of the implant holder 608B, 608C and the implant 10, 12 in a specific orientation or at a specific height. In addition, any motion of the moveable marker 806 could be used for other variable attributes of any other type of navigated implant.

Although depicted and described with respect to linear movement of the moveable marker 806, the moveable marker 806 should not be limited to just sliding as there may be applications where rotation of the marker 806 or other movements could be useful to provide information about the implant 10, 12. Any relative change in position between the set of fixed markers 804 and the moveable marker 806 could be relevant information for the implant 10, 12 or other device. In addition, although expandable and articulating implants 10, 12 are exemplified, the instrument 608 could work with other medical devices and materials, such as spacers, cages, plates, fasteners, nails, screws, rods, pins, wire structures, sutures, anchor clips, staples, stents, bone grafts, biologics, cements, or the like.

Figure 19A:
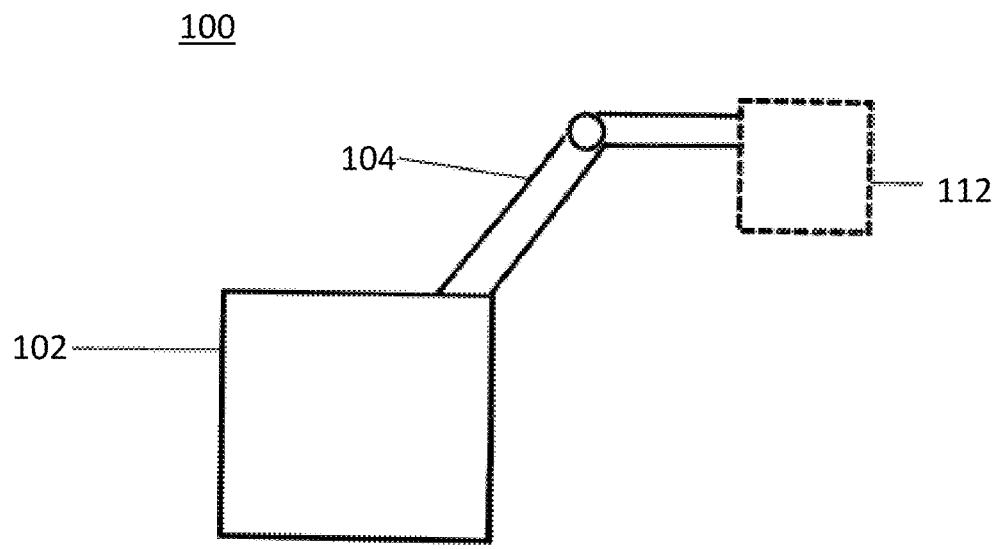
FIG. 19A depicts an embodiment of a robot with interchangeable or alternative end-effectors.

Turning now to FIG. 19A, it is envisioned that the robot end-effector 112 is interchangeable with other types of end-effectors 112. Moreover, it is contemplated that each end-effector 112 may be able to perform one or more functions based on a desired surgical procedure. For example, the end-effector 112 having a guide tube 114 may be used for guiding an instrument 608 as described herein. In addition, end-effector 112 may be replaced with a different or alternative end-effector 112 that controls a surgical device, instrument, or implant, for example.

The alternative end-effector 112 may include one or more devices or instruments coupled to and controllable by the robot. By way of non-limiting example, the end-effector 112, as depicted in FIG. 19A, may comprise a retractor (for example, one or more retractors disclosed in U.S. Pat. Nos. 8,992,425 and 8,968,363) or one or more mechanisms for inserting or installing surgical devices such as expandable intervertebral fusion devices (such as expandable implants exemplified in U.S. Pat. Nos. 8,845,734; 9,510,954; and 9,456,903), stand-alone intervertebral fusion devices (such as implants exemplified in U.S. Pat. Nos. 9,364,343 and 9,480,579), expandable corpectomy devices (such as corpectomy implants exemplified in U.S. Pat. Nos. 9,393,128 and 9,173,747), articulating spacers (such as implants exemplified in U.S. Pat. No. 9,259,327), facet prostheses (such as devices exemplified in U.S. Pat. No. 9,539,031), laminoplasty devices (such as devices exemplified in U.S. Pat. No. 9,486,253), spinous process spacers (such as implants exemplified in U.S. Pat. No. 9,592,082), inflatables, fasteners including polyaxial screws, uniplanar screws, pedicle screws, posted screws, and the like, bone fixation plates, rod constructs and revision devices (such as devices exemplified in U.S. Pat. No. 8,882,803), artificial and natural discs, motion preserving devices and implants, spinal cord stimulators (such as devices exemplified in U.S. Pat. No. 9,440,076), and other surgical devices. The end-effector 112 may include one or instruments directly or indirectly coupled to the robot for providing bone cement, bone grafts, living cells, pharmaceuticals, or other deliverable to a surgical target. The end-effector 112 may also include one or more instruments designed for performing a discectomy, kyphoplasty, vertebrostenting, dilation, or other surgical procedure.

The end-effector itself and/or the implant, device, or instrument may include one or more markers 118 such that the location and position of the markers 118 may be identified in three-dimensions. It is contemplated that the markers 118 may include active or passive markers 118, as described herein, that may be directly or indirectly visible to the cameras 200. Thus, one or more markers 118 located on an implant 10, for example, may provide for tracking of the implant 10 before, during, and after implantation.

Figure 19B:
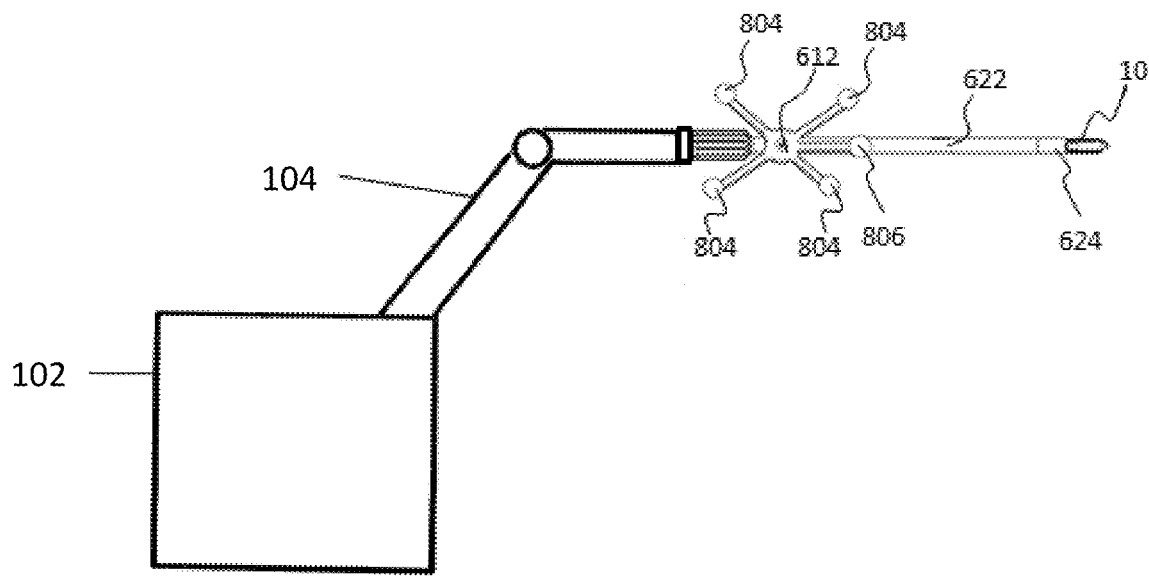
FIG. 19B depicts an embodiment of a robot with an instrument style end-effector coupled thereto.

As shown in FIG. 19B, the end-effector 112 may include an instrument 608 or portion thereof that is coupled to the robot arm 104 (for example, the instrument 608 may be coupled to the robot arm 104 by the coupling mechanism shown in FIGS. 9A-9C) and is controllable by the robot system 100. Thus, in the embodiment shown in FIG. 19B, the robot system 100 is able to insert implant 10 into a patient and expand or contract the expandable implant 10. Accordingly, the robot system 100 may be configured to assist a surgeon or to operate partially or completely independently thereof. Thus, it is envisioned that the robot system 100 may be capable of controlling each alternative end-effector 112 for its specified function or surgical procedure.

System with Surgical Implant Planning Computer and Surgical Robotic System

Figure 20:
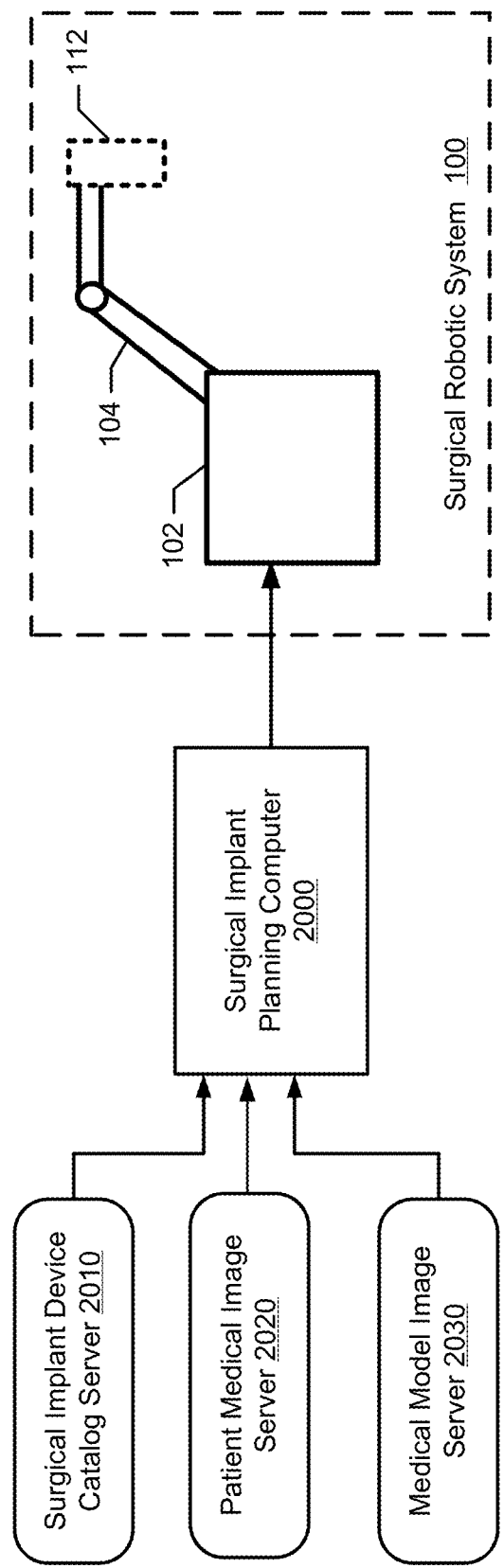
FIG. 20 illustrates a block diagram of a surgical system including a surgical implant planning computer connected to a surgical robotic system that operate in accordance with some exemplary embodiments.

FIG. 20 illustrates a block diagram of a surgical system that includes a surgical implant planning computer 2000 connected to a surgical robotic system 100 and which are configured to operate in accordance with some embodiments. The surgical implant planning computer 2000 can be connected to a surgical implant device catalog server 2010 to obtain information that defines available types and characteristics of surgical implant devices, such as different dimensional bone screws, and can be further connected to obtain images from a patient medical image server 2020 and may be connected to obtain anatomical model images from a medical model image server 2030.

Referring to FIG. 20, the surgical implant planning computer 2000 allows auto-generation of a surgical plan with respect to an initial medical image and/or uses a surgical plan developed by a surgeon for implanting a surgical implant device with respect to the initial medical image. The surgical implant planning computer 2000 automatically transforms the surgical plan for use in implanting the surgical implant device into a bone that is shown in a target medical image. The surgical implant planning computer 2000 may provide the transformed surgical plan to the surgical robotic system 100 to control movement of a surgical end-effector 112 by the surgical robotic system to position the surgical end-effector 112 relative to a location on a bone of the patient to facilitate implantation of the surgical implant device into the bone.

In one example embodiment, a surgeon can interface with the surgical implant planning computer 2000 to generate a surgical plan for the locations of bone screws on a representative scan or image (collectively referred to as a "medical image", "image scan", and "image" for brevity) of a bone in which the screws are to be inserted. The surgical implant planning computer 2000 can obtain an initial image of a normal spine, possibly from a subject of a specific or average height, age and weight, from the patient medical image server 2020, e.g., CT scan of a patient's spine, or may obtain a modeled initial image of the appropriate anatomical structure from the medical model image server 2030 which may have images that are based on, e.g., Sawbones model by Pacific Research, Inc. A surgical plan can be generated that identifies where screws can be implanted at any foreseeable location relative to a bone shown in the initial image where a screw might be foreseeably needed. This surgical plan can be generated automatically by an algorithm that considers locations of available bony corridors through image processing, or manually by an individual who is knowledgeable about appropriate surgical placement of screws. For example, in an image scan of the thoracolumbosacral spine, a surgical plan can be generated by a surgeon scrolling through an image volume and marking locations that identify where pedicle screws could be implanted in every pedicle from T1-S3 in the image. The initial image and the surgical plan identifying corresponding screw locations are stored by the surgical implant planning computer 2000 in a local or remote memory database for later recall and use with a particular identified patient or, more generally, future new patients.

When a new target image for a patient is received and screw planning is needed, the surgeon would interface with the surgical implant planning computer 2000 to specify where screws are to be inserted in one or more regions of a bone shown in the target image. The computer 2000 responsively obtains the initial image, the surgical plan, and the target image, and performs spatial transformations to morph the contours of the initial image to sufficiently match, according to a defined rule, the contours of the target image at the specified locations. To minimize the amount of morphing required, the initial image retrieved from the patient medical image server 2020 or medical model image server 2030 may be selected to match the age, gender, height, weight, ethnicity or other parameters of the target image to provide a closer approximation. Different sections of the images could be morphed with different transformations so that each specific bone of interest from the initial image sufficiently matches the target image, such as according to a best-fit operation. For example, if trying to match three levels of the lumbar spine from the initial image to the corresponding three levels in the target image, the computer 2000 may operate to independently transform each vertebra of the initial image to best match each corresponding vertebra shown in the target image. Moreover, within a bone different portions around key points could be stretched and rotated differently to satisfy the defined rule for conformance between corresponding portions in the initial and target images. Operations for transforming, e.g., morphing, may include affine transformations, which do not require the body being morphed to maintain a constant aspect ratio.

Figure 21:
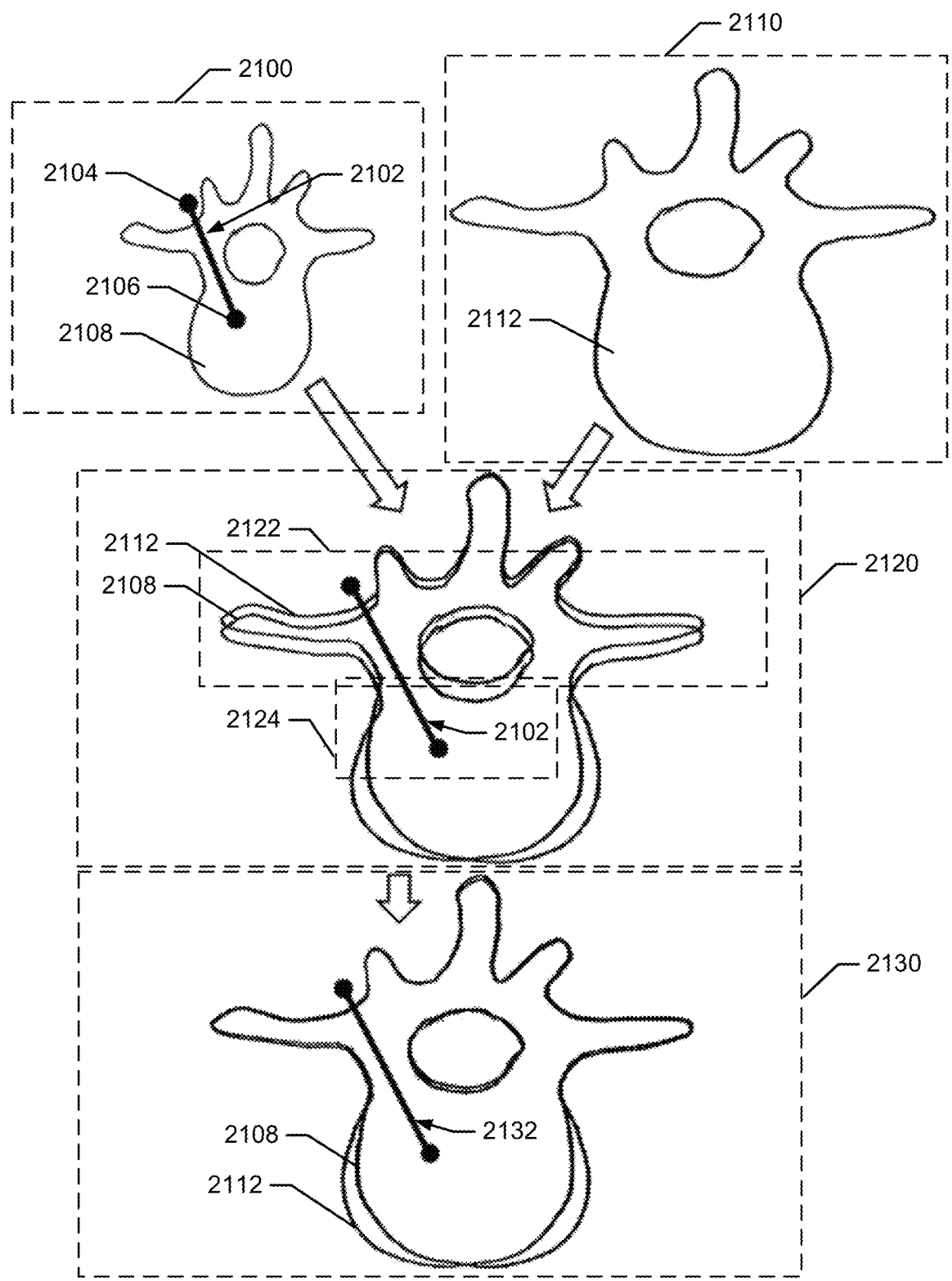
FIG. 21 depicts a set of images that can be displayed on a display device and related operations performed by the surgical implant planning computer to generate a transformation matrix that transforms a surgical plan for implanting a surgical implant device relative to a bone in an initial image for overlay on a bone in a target image, in accordance with some exemplary embodiments.

FIG. 21 depicts a set of images that can be displayed on a display device and related operations performed by the surgical implant planning computer 2000 to generate a transformation matrix that transforms a surgical plan for implanting a surgical implant device relative to a bone in an initial image for overlay on a bone in a target image, in accordance with some exemplary embodiments.

Referring to FIG. 21, the images include an initial image 2100, a target image 2110, an initial overlaid composite view 2120 of the initial and target images 2100 and 2110 in which only total horizontal scaling, total vertical scaling, rotation and translation are allowed, and a transformed overlaid composite view 2130 of the target image 2110, which has been further asymmetrically transformed in subsets of the image to better conform to the initial image 2100. The initial image 2100 shows a bone 2108 and an initial surgical plan for where a tip location 2106 and tail location 2104 of a surgical screw 2102 are to be located after implantation into the bone 2108. As explained above, the initial surgical plan shown in initial image 2100 may have been developed by a surgeon viewing the bone 2108 in the initial image 2100 of the patient or another patient (e.g., from patient medical image server 2020) or medical model (e.g., from medical model image server 2030), or may have been automatically generated by the surgical implant planning computer 2000 with respect to the bone 2108 shown in the initial image 2100 while operating to satisfy one or more rules generated based on the surgeon's earlier defined preferences regarding screw or other device placement (preferred depth, preferred angle, etc.) relative to defined and/or determined characteristics of the bone 2108. The initial image 2100 is noticeably smaller than the target image 2110 and to achieve the initial overlay 2120 initial image 2100 is scaled so that the total anteroposterior and lateral dimensions match those of the target image 2110.

As will be explained below, the surgical implant planning computer 2000 further asymmetrically transforms the implant locations within key anatomic regions 2122 defined by the surgical plan for use with the bone 2112 shown in the target image 2110 of a patient obtained by CT scan, x-ray, or other medical imaging process. The transformed implant locations, e.g., the transformed tip and tail locations of the surgical screw 2132, may be provided to the surgical robotic system 100 to control movement of the surgical end-effector 112 by the surgical robotic system 100 to position the surgical end-effector 112 relative to a bone of the patient to facilitate implantation of the surgical screw 2132 in the bone.

Figure 22:
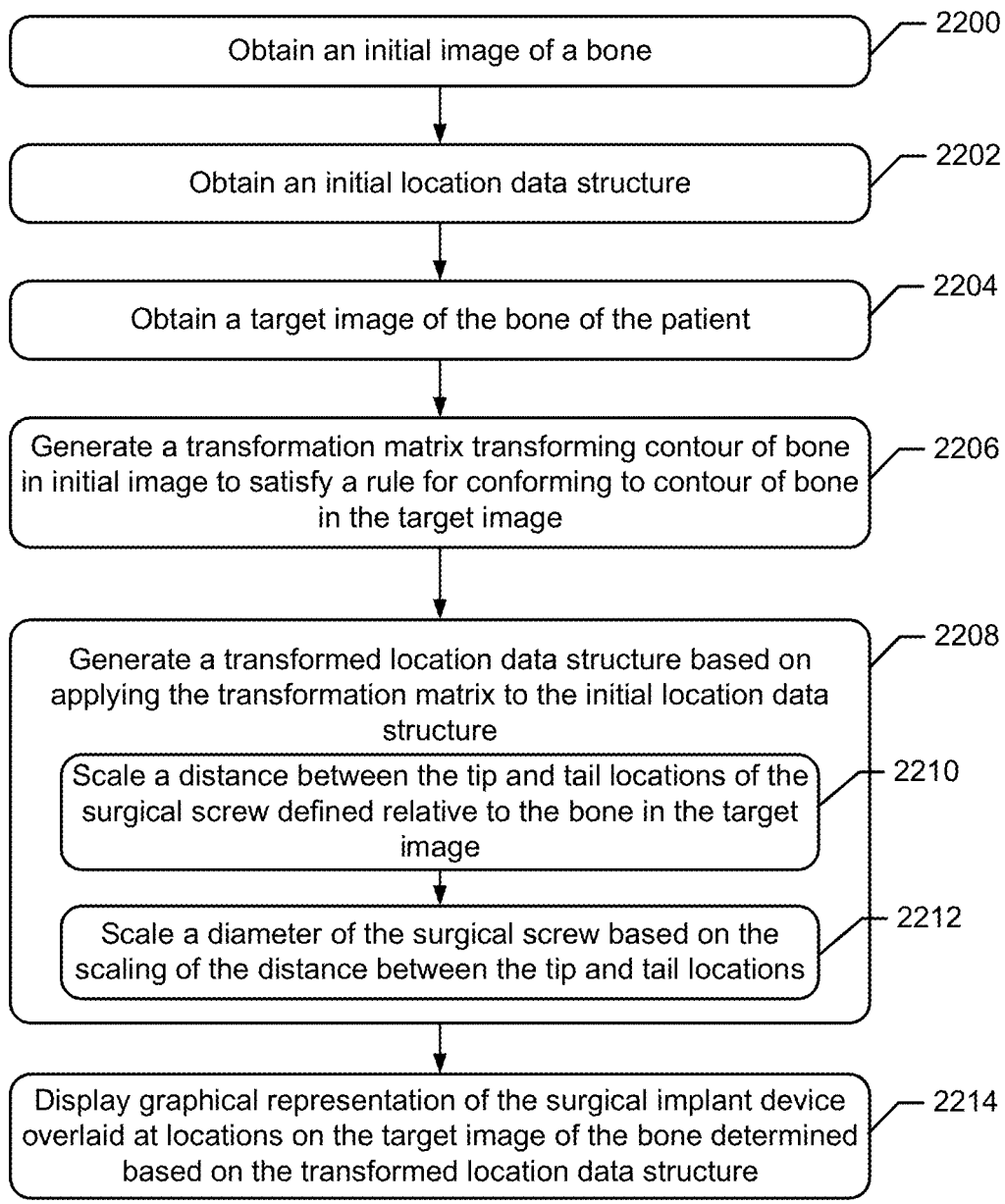
FIGS. 22 and 23 illustrate flowcharts of operations by the surgical implant planning computer in accordance with some exemplary embodiments.
Figure 23:
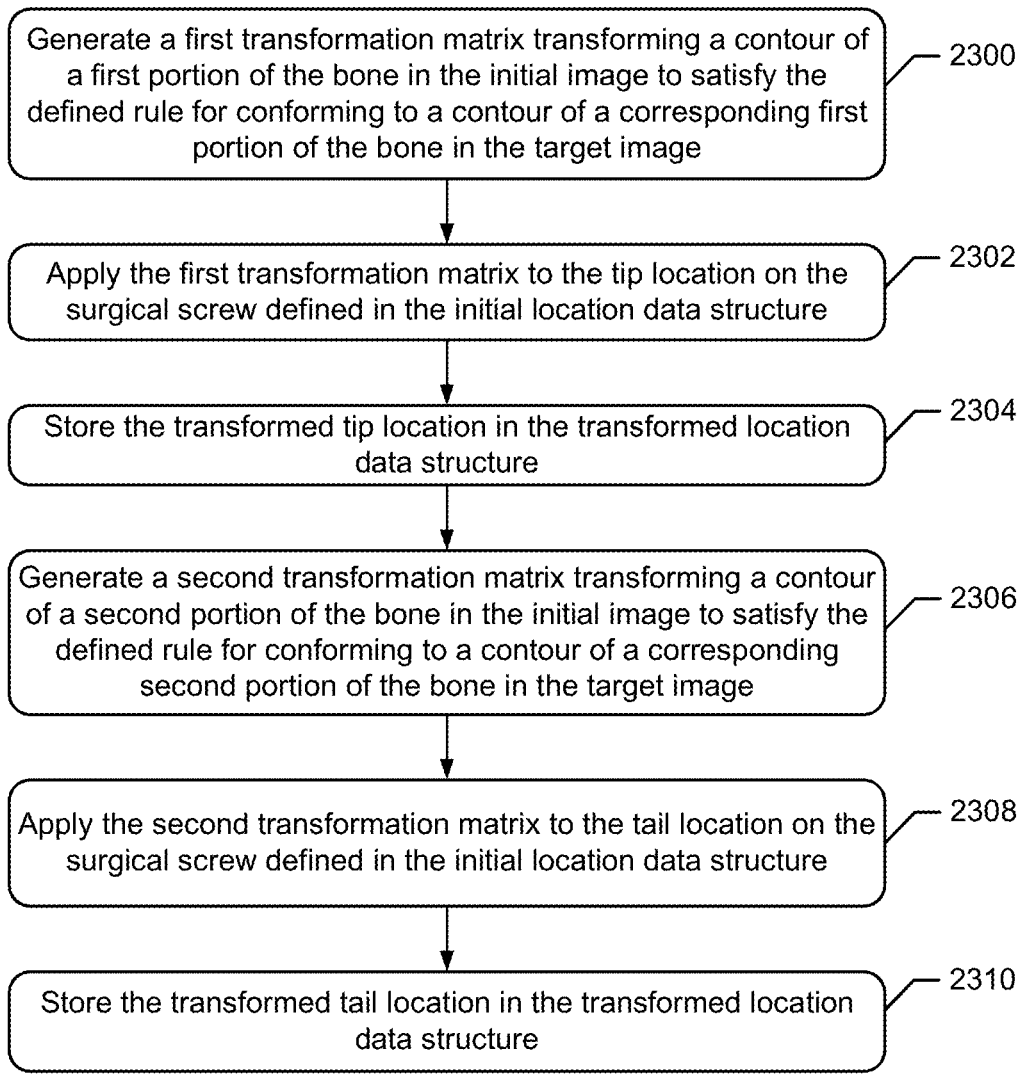

FIGS. 22 and 23 illustrate flowcharts of operations by the surgical implant planning computer 2000 for generating and using a transformation matrix for surgical planning in accordance with some exemplary embodiments Referring to FIGS. 21 and 22, the computer 2000 obtains 2200 the initial image 2100 of the bone and obtains 2202 an initial location data structure containing data defining mapping between a set of locations on the surgical implant device, e.g., tip 2106 and tail 2104 on screw 2102, and a corresponding set of locations where they are overlaid relative to the bone 2108 in the initial image 2100. Locations of the tip and the tail of the surgical screw 2102 relative to the bone 2108 in the initial image 2100 can be determined based on the data in the initial location data structure. The type of surgical implant device and associated locations (e.g., tip, tail, other defined locations and/or contours) that are to be mapped to an initial image may be obtained from the surgical implant device catalog server 2010, and the initial image may be obtained from the medical model image server 2030 and/or the patient medical image server 2020. The computer 2000 also obtains 2204 the target image 2110 of the patient's bone 2112 from the patient medical image server 2020.

The computer 2000 generates 2206 a transformation matrix that transforms a contour of a portion 2122 of the bone 2108 in the initial image 2100 to satisfy a defined rule for conforming to a contour of a corresponding portion of the bone 2112 in the target image 2110, where an example portion of the overlaid images 2120 is illustrated as 2112 in FIG. 21. The transformation matrix may be generated based on how much groups of points defining a surface contour of the bone 2108 in the portion 2122 of the initial image 2100 need to be individually moved or collectively stretched and/or rotated to satisfy the defined rule for conforming to a corresponding surface contour of the bone 2112 in the portion 2122 of the target image 2110. The defined rule may correspond to morphing the bone 2108 to achieve an optimal fit of the respective surface contours of the bone 2112 within the portion 2122. Operations for morphing include, without limitation, affine transformations, which do not require the body being morphed to maintain a constant aspect ratio.

The overlaid composite image 2120 may be generated by transforming, e.g., stretching, the bone 2108 in the initial image 2100 to approximately have the same overall size as the bone 2112 in the target image 2110. The transformed overlaid composite view 2130 may be generated by further transforming, e.g., morphing through stretching and rotating, a plurality of contours along anterior and posterior external surfaces and spinal canal surfaces of the bone 2108 in the initial image 2110 to more closely conform to the corresponding contours of the bone 2112 in the target image 2110.

The computer 2000 then generates 2208 a transformed location data structure based on applying the transformation matrix to the initial location data structure of the surgical implant device, e.g., screw 2102, or applying the transformation matrix to key points of the initial location data structure such as screw tip 2106 and screw tail 2104. This distinction is made because transforming the entire screw, which crosses two regions 2122 and 2124 that are differently transformed, could result in a bent screw 2132 whereas transforming the tip and tail points only and then re-connecting these points with a straight line would result in a straight screw 2132. The computer 2000 displays 2214 on a display device a graphical representation of the surgical implant device, e.g., screw 2132, overlaid at locations on the bone 2112 in the target image 2110 that are determined based on the transformed location data structure.

In one embodiment, the surgical implant planning computer 2000 can be configured to display auto-planned screw locations on the target image of the patient for the surgeon to view and adjust if needed. The computer 2000 automatically determines a length of the screw based on the known screw tip and tail coordinates defined based on dimensions of the bone 2108 and based on characteristic data for available screws that is obtained from the surgical implant device catalog server 2010. The computer 2000 may be configured to automatically scale the diameter of the screw based on the determined scaling that occurs between the original screw length relative to the bone in the initial image 2100 to the transformed screw length relative to the bone 2112 in the target image 2110. For example, if a 50 mm screw fit the bone 2108 in the initial image 2100 but after transformation of the bone 2108 to conform to the bone 2112, the screw length was reduced to 40 mm, this reduction would represent a decrease of 20% of the screw length. The computer 2000 may be configured to correspondingly reduce the screw diameter by 20%. Alternatively or additionally, the computer 2000 may access a historical repository of data provided for a group of actual patients with different lengths of screws that identifies what screw diameter was selected for use with corresponding various lengths of screws for various defined regions of bone. Alternatively or additionally, the computer 2000 can use the known information about the locations of bone contours of the target image 2110 which are evaluated during transformation of the initial image 2100 for surface conformance, the amount of space available within the region through which the screw passes can be automatically measured and a best fitting diameter of screw automatically selected.

In an illustrative embodiment, the surgical screw 2102 has a tip location and a tail location defined by the initial location data structure relative to the bone in the initial image, and the computer 2000 scales (2210 in FIG. 22) a distance between the tip and tail locations of the surgical screw defined relative to the bone 2108 in the target image 2100 based on the transformation matrix. In a further embodiment, the computer 2000 scales (2212 in FIG. 22) a diameter of the surgical screw based on the scaling of the distance between the tip and tail locations of the surgical screw.

As explained above, contours along key points in different portions on a bone can be stretched and rotated differently to satisfy the defined rule for conformance between corresponding portions in the initial and target images. In FIG. 21 another portion 2124 within the overlaid images 2120 is illustrated in which the contours of the bone 2108 can be transformed to more closely conform to the corresponding contours of the bone 2112 in the target image 2110 also within the portion 2124. The same or another transformation matrix can be generated or refined based on the transformations performed within the portion 2124 of the overlaid images 2120. For example, it may be desirable for good pedicle screw placement to fit the initial image shape to the target image shape in the posterior region of a vertebra in such a way that the pedicle widths overlay while also maintaining the size of the spinal canal and offset of pedicles from midline. Such a goal may require different portions of the vertebra to be transformed with a different transformation matrix and may disallow usage of a single transformation matrix for the entire vertebra.

A generalized method for transforming individual regions of an initial image to match corresponding regions of a target image while maintaining continuity at the boundaries between regions can be applied using a technique similar to that used to digitally create animated videos in which images are morphed (see for example http://www.learnopencv.com/face-morph-using-opencv-cpp-python/). This morphing technique uses sets of points with correspondence of landmarks from the initial image to the target image, divides the image area or volume into discrete regions using Delaunay Triangulation, and then applies affine transformations to each triangle (2D) or tetrahedron (3D) to fit each triangulated area or volume from the initial to a target image. In the current application, for example, to match an initial image volume of an ideal spine to a target image volume of a new patient's spine, key landmarks such as the spinous process, lamina, transverse process, pedicle, and vertebral body could be automatically identified in initial and target images through pattern recognition and image processing or manually identified by a user scrolling through the image and marking these locations to create the point correspondence set. Delaunay Triangulation and affine transformations for best fit could be automatically generated using known techniques. The affine transformations corresponding to the tetrahedra within which the tip and tail points lie would then be applied to the tip and tail points of a screw. The screw body is not transformed since doing so might alter its cylindrical shape. Instead, a new screw body would be positioned using the transformed tip and tail points to achieve the target screw plan.

In some further embodiments, the operations for generating 2206 the transformation matrix can include modifying a size and/or a rotational angle of the contour of the portion of the bone 2108 in the initial image 2100 to satisfy the defined rule for conforming to a size and/or a rotational angle of the contour of the corresponding portion of the bone 2112 in the target image 2110. Moreover, as explained above, the operations can be repeated to modify the size and/or the rotational angle of contours of a plurality of portions of the bone 2108 in the initial image 2100 to satisfy the defined rule for conforming to the size and/or the rotational angle of contours of a corresponding plurality of portions of the bone 2112 in the target image 2110.

In one further embodiment, the operations for modifying the size and/or the rotational angle of the contour of the portion of the bone 2108 in the initial image 2100, can include applying a best fit transformation of the size and/or the rotational angle of the contour of the portion of the bone 2108 in the initial image 2100 to satisfy the defined rule for conforming to the size and/or the rotational angle of the contour of the corresponding portion of the bone 2112 in the target image 2110, such as shown in the overlay composite image 2120 and/or the further transformed overlay composite image 2130. In another further embodiment, the operations for modifying the size and/or the rotational angle of the contour of the portion of the bone 2108 in the initial image 2100, can include applying an affine transformation of the size and/or the rotational angle of the contour of the portion of the bone 2108 in the initial image 2100 to satisfy the defined rule for conforming to the size and/or the rotational angle of the contour of the corresponding portion of the bone 2112 in the target image 2110.

In a further embodiment, the operations for generating the transformed location data structure based on applying the transformation matrix to the initial location data structure can include, for a first one of the locations on the surgical implant device defined in the initial location data structure, applying the transformation matrix to transform a corresponding first one of the locations defined by the initial location data structure relative to the bone 2108 in the initial image 2100 to a transformed first location defined relative to the bone 2112 in the target image 2110, and storing the transformed first location in the transformed location data structure with an association to the first one of the locations on the surgical implant device.

The operations can further include generating another transformation matrix that transforms a contour of another portion 2124 of the bone 2108 in the initial image 2100 to satisfy the defined rule for conforming to a contour of a corresponding another portion 2124 of the bone 2112 in the target image 2110. The operations for generating the transformed location data structure based on applying the transformation matrix to the initial location data structure can further include, for a second one of the locations on the surgical implant device defined in the initial location data structure, applying the other transformation matrix to transform a corresponding second one of the locations defined by the initial location data structure relative to the bone 2108 in the initial image 2100 to a transformed second location defined relative to the bone 2112 in the target image 2110, and storing the transformed second location in the transformed location data structure with an association to the second one of the locations on the surgical implant device.

Reference is now made to the flowchart of FIG. 23 which illustrates example operations that can be performed to transform the mapping of locations on the screw 2102 to the bone 2108 shown in the initial image 2100 to a corresponding mapping of locations on the screw 2102 to the bone 2112 shown in the target image 2110. A first transformation matrix is generated 2300 that transforms a contour of a first portion of the bone 2108 in the initial image 2100 to satisfy a defined rule for conforming to a contour a corresponding first portion of the bone 2112 in the target image 2110. The first transformation matrix is applied 2302 to the tip location on the surgical screw defined in the initial location data structure. The transformed tip location is then stored 2304 in the transformed location data structure. A second transformation matrix is generated 2306 that transforms a contour of the second portion of the bone 2108 in the initial image 2100 to satisfy a defined rule for conforming to a contour of a corresponding second portion of the bone 2112 in the target image 2110. The second transformation matrix is applied 2308 to the tail location on the surgical screw defined in the initial location data structure, and the transformed tail location is then stored 2310 in the transformed location data structure.

Some scenarios can be envisioned where the operations for automatically generating a surgical plan for implanting a screw or other device into a patient's bone using an anatomical model may not provide an acceptable solution for some patients. For example, a corridor of bone can be a straight connection between locations where the tip and tail of a screw would be positioned in the initial image (e.g., corresponding to an anatomical model or other patient), however the corresponding corridor of patient's bone in the target image of the patient may be excessively curved. Various such scenarios are depicted in the images of bones shown in FIG. 24, where a surgical implant device, e.g., screw, is displayed as an overlay on the bones.

Figure 24:
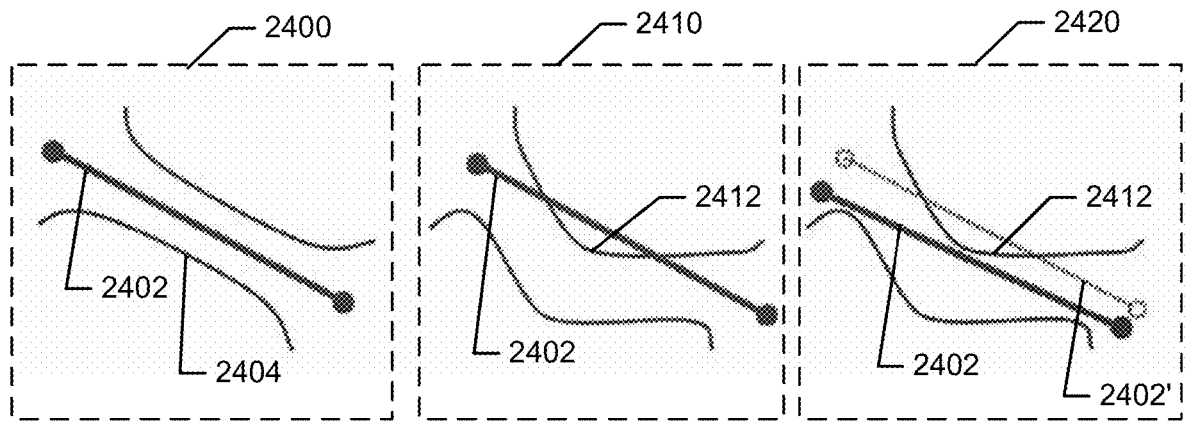
FIG. 24 depicts a set of images of bones with an overlaid surgical implant device that can be displayed on a display device via operations in accordance with some exemplary embodiments.

Referring to FIG. 24, image 2400 illustrates a bone 2404 having a straight corridor in which a screw, rod, or other device 2402 can be implanted. In sharp contrast, image 2410 illustrates a bone 2412 having a substantially curved corridor in which the implant device 2402 could be implanted. However, it would not be medically acceptable to implant device 2402 where it penetrates a surface of and extends outside the bone 2412 through the curved region. In accordance with embodiments herein, the surgical implant planning computer 2000 can be configured to identify and compensate for such curved regions, by adjusting the location of the implant device 2402 to extend entirely within the bone 2412. In the example of image 2420, the computer 2000 shifts inward the location of the implant device 2402 from location 2402' so as to not extend outside the bone 2412 when generating the surgical plan for locations where the device 2402 is to be implanted within the bone 2412.

Figure 25:
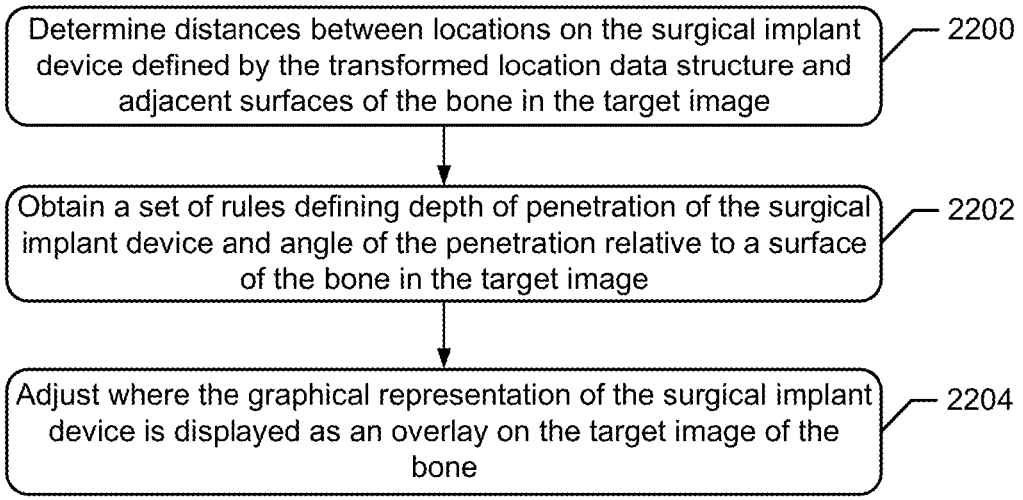
FIG. 25 illustrate flowcharts of operations by the surgical implant planning computer to adjust a location of a surgical implant device relative to the bones in the images depicted in FIG. 24, in accordance with some exemplary embodiments.

FIG. 25 is a flowchart of corresponding operations that the surgical implant planning computer 2000 may perform to compensate for bone curvature or other bone recesses when generating a surgical plan. Referring to FIG. 25, distances are determined 2200 between locations on the surgical implant device defined by the transformed location data structure and adjacent surfaces of the bone in the target image. Responsive to the determined distances, the computer 2000 adjusts 2204 where the graphical representation of the surgical implant device is displayed as an overlay on the target image of the bone.

The operations for generating the surgical plan can include biasing or constraining the location of the implant device based on rules that are defined based on preferences of a surgeon. The computer 2000, may obtain 2202 a set of rules defining depth of penetration of the surgical implant device and angle of the penetration relative to a surface of the bone in the target image, and use the set of rules to adjust 2204 where the graphical representation of the surgical implant device is displayed as an overlay on the target image of the bone. For example, some surgeons may prefer to have pedicle screws at the lower lumbar level be implanted directed straight in from posterior to anterior while other surgeons may prefer to have the screws implanted angled inward from lateral to medial. Alternatively or additionally, some surgeons may prefer to have pedicle screws penetrate to 50% of the depth of the vertebral body while other surgeons may prefer to have pedicle screws penetrate to 75% of the depth of the vertebral body. These and other preferences of surgeons on screw placement and other preferences for implant devices, can be stored with the surgical plan that the surgeon makes relative to the initial image, and which is used by the computer 2000 during the transformation of the surgical plan to be directed to the target image. The computer 2000 may enable surgeons who prefer not to go through the process of planning every foreseeable screw and/or other device implant location, to instead select from a defined set (e.g., a diagram) of possible choices that most closely match their identified preferences.

In this manner, a surgical system is provided that transforms an automatically generated predictive surgical plan and/or the surgeon's initial surgical plan made with respect to an initial medical image to a transformed plan for use in implanting the surgical implant device into a patient's bone that is shown in a target medical image. Such automatic planning can reduce the time required for the surgery and increase precision of planning. The transformed surgical plan can be displayed for review by the surgeon and/or can be provided to a surgical robotic system to control positioning of a surgical end-effector of the surgical robotic system relative to the bone of the patient.

Although the robot and associated systems described herein are generally described with reference to spine or other bone applications, it is also contemplated that the surgical system is configured for use in other surgical applications, including but not limited to, surgeries in trauma or other orthopedic applications (such as the placement of intramedullary nails, plates, and the like), cranial, neuro, cardiothoracic, vascular, colorectal, oncological, dental, and other surgical operations and procedures.

Components of Surgical Implant Planning Computer

Figure 26:
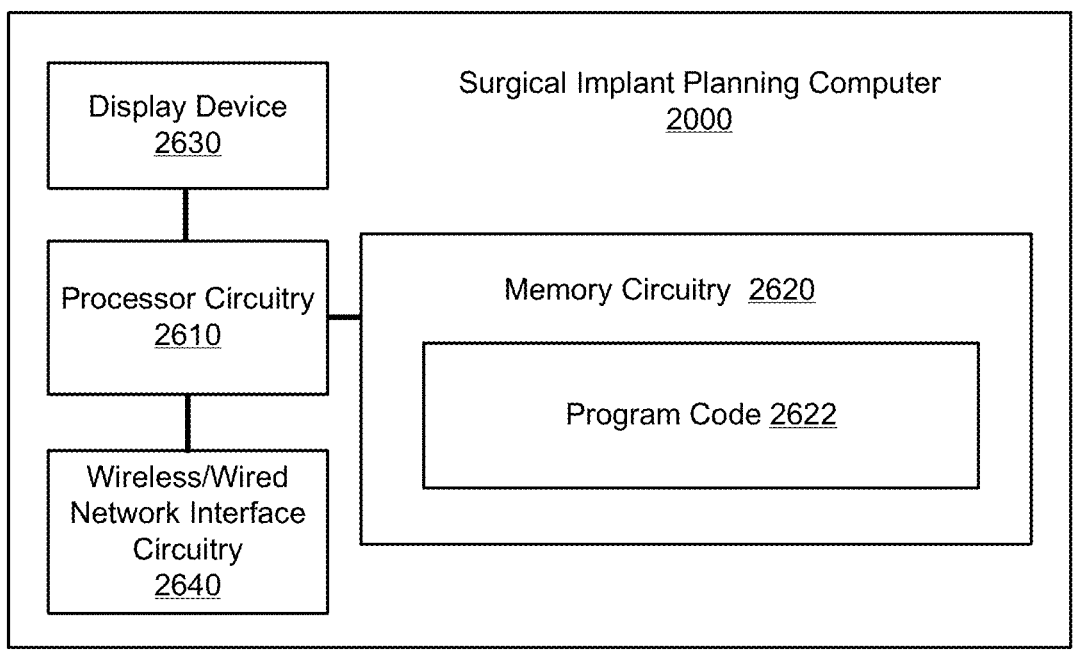
FIG. 26 illustrates a block diagram of components of a surgical implant planning computer that are configured to operate in accordance with some exemplary embodiments.

FIG. 26 illustrates a block diagram of components of a surgical implant planning computer 2000 that are configured to operate in accordance with some exemplary embodiments. The computer 2000 can include a display device 2630, a wireless and/or wired network interface circuit 2640, at least one processor circuit 2610 (processor), and at least one memory circuit 2620 (memory). The processor 2610 is connected to the memory 2620, the display device 2630, and the network interface circuit 2640. The memory 2620 stores program code 2622 that is executed by the processor 2610 to perform operations. The processor 2610 may include one or more data processing circuits, such as a general purpose and/or special purpose processor (e.g., microprocessor and/or digital signal processor), which may be collocated or distributed across one or more data networks. The processor 2610 is configured to execute computer program instructions among program code 2622 in the memory 2620, described below as a computer readable medium, to perform some or all of the operations and methods for one or more of the embodiments disclosed herein for a surgical implant planning computer 2000. The network interface circuit 2640 is configured to communicate with another electronic device, such as the servers 2010, 2020, and/or 2030, and the surgical robotic system 100, through a wired network (e.g., ethernet, USB, etc.) and/or wireless network (e.g., Wi-Fi, Bluetooth, cellular, etc.).

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a non-transitory computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

What is claimed is:

1. A method by a surgical implant planning computer for positioning a surgical implant device relative to a bone of a patient, the method comprising:
    obtaining an initial image of a bone;
    obtaining an initial location data structure containing data defining mapping between a set of locations on the surgical implant device and a corresponding set of locations relative to the bone in the initial image;
    obtaining a target image of the bone of the patient;
    generating a transformation matrix that transforms a contour of a portion of the bone in the initial image to satisfy a defined rule for conforming to a contour of a corresponding portion of the bone in the target image;
    generating a transformed location data structure based on applying the transformation matrix to the initial location data structure; and
    displaying a graphical representation of the surgical implant device overlaid at locations on the target image of the bone determined based on the transformed location data structure.

2. The method of claim 1, wherein the surgical implant device comprises a surgical screw, and further comprising:
    determining locations of a tip and a tail of the surgical screw relative to the bone in the initial image based on the data in the initial location data structure.

3. The method of claim 1, wherein the generation of the transformation matrix comprises:
    modifying a size and/or a rotational angle of the contour of the portion of the bone in the initial image to satisfy the defined rule for conforming to a size and/or a rotational angle of the contour of the corresponding portion of the bone in the target image.

4. The method of claim 3, further comprising:
    repeating the modification of the size and/or the rotational angle of contours of a plurality of portions of the bone in the initial image to satisfy the defined rule for conforming to the size and/or the rotational angle of contours of a corresponding plurality of portions of the bone in the target image.

5. The method of claim 3, wherein the modification of the size and/or the rotational angle of the contour of the portion of the bone in the initial image, comprises:
    applying a best fit transformation of the size and/or the rotational angle of the contour of the portion of the bone in the initial image to satisfy the defined rule for conforming to the size and/or the rotational angle of the contour of the corresponding portion of the bone in the target image.

6. The method of claim 3, wherein the modification of the size and/or the rotational angle of the contour of the portion of the bone in the initial image, comprises:
    applying an affine transformation of the size and/or the rotational angle of the contour of the portion of the bone in the initial image to satisfy the defined rule for conforming to the size and/or the rotational angle of the contour of the corresponding portion of the bone in the target image.

7. The method of claim 1, wherein the generation of the transformed location data structure based on applying the transformation matrix to the initial location data structure, comprises:
    for a first one of the locations on the surgical implant device defined in the initial location data structure, applying the transformation matrix to transform a corresponding first one of the locations defined by the initial location data structure relative to the bone in the initial image to a transformed first location defined relative to the bone in the target image; and
    storing the transformed first location in the transformed location data structure with an association to the first one of the locations on the surgical implant device.

8. The method of claim 7, further comprising:
    generating another transformation matrix that transforms a contour of another portion of the bone in the initial image to satisfy the defined rule for conforming to a contour of a corresponding another portion of the bone in the target image,
    wherein the generation of the transformed location data structure based on applying the transformation matrix to the initial location data structure, further comprises:
        for a second one of the locations on the surgical implant device defined in the initial location data structure, applying the other transformation matrix to transform a corresponding second one of the locations defined by the initial location data structure relative to the bone in the initial image to a transformed second location defined relative to the bone in the target image; and
        storing the transformed second location in the transformed location data structure with an association to the second one of the locations on the surgical implant device.

9. The method of claim 7, wherein:
    the surgical implant device comprises a surgical screw having a tip location and a tail location defined in the initial location data structure relative to the bone in the initial image; and
    the generation of the transformed location data structure based on applying the transformation matrix to the initial location data structure, comprises:
        generating a first transformation matrix that transforms a contour of a first portion of the bone in the initial image to satisfy the defined rule for conforming to a contour of a corresponding first portion of the bone in the target image;
        for the tip location on the surgical screw defined in the initial location data structure, applying the first transformation matrix to transform a corresponding first location defined by the initial location data structure relative to the bone in the initial image to a transformed first location defined relative to the bone in the target image;
        storing the transformed first location in the transformed location data structure with an association to the tip location on the surgical screw;
        generating a second transformation matrix that transforms a contour of a second portion of the bone in the initial image to satisfy the defined rule for conforming to a contour of a corresponding second portion of the bone in the target image,
        for the tail location on the surgical screw defined in the initial location data structure, applying the second transformation matrix to transform a corresponding second location defined by the initial location data structure relative to the bone in the initial image to a transformed second location defined relative to the bone in the target image; and
        storing the transformed second location in the transformed location data structure with an association to the tail location on the surgical screw.

10. The method of claim 1, wherein:
the surgical implant device comprises a surgical screw having a tip location and a tail location defined by the initial location data structure relative to the bone in the initial image; and
the generation of the transformed location data structure based on applying the transformation matrix to the initial location data structure, comprises scaling a distance between the tip and tail locations of the surgical screw defined relative to the bone in the target image based on the transformation matrix.

11. The method of claim 10, wherein the generation of the transformed location data structure based on applying the transformation matrix to the initial location data structure, further comprises:
scaling a diameter of the surgical screw based on the scaling of the distance between the tip and tail locations of the surgical screw.

12. The method of claim 1, further comprising:
providing the transformed location data structure to a surgical robotic system to control positioning of a surgical end-effector of the surgical robotic system relative to a location on the bone of the patient based on data of the transformed location data structure.

13. The method of claim 12, further comprising:
transforming locations that are defined by the transformed location data structure in a reference coordinate system of the target image of the bone to another reference coordinate system of the surgical end-effector;
controlling movement by the surgical robotic system of the surgical end-effector to position the surgical end-effector relative to the location on the bone of the patient based on the transformed locations to facilitate implantation of the surgical implant device in the bone of the patient.

14. The method of claim 1, further comprising:
determining distances between locations on the surgical implant device defined by the transformed location data structure and adjacent surfaces of the bone in the target image; and
responsive to the determined distances, adjusting where the graphical representation of the surgical implant device is displayed as an overlay on the target image of the bone.

15. The method of claim 1, further comprising:
obtaining a set of rules defining depth of penetration of the surgical implant device and angle of the penetration relative to a surface of the bone in the target image; and
responsive to the set of rules, adjusting where the graphical representation of the surgical implant device is displayed as an overlay on the target image of the bone.

16. A surgical implant planning computer comprising:
at least one network interface connected to at least one networked server;
a display device;
at least one processor connected to the at least one network interface and the display device; and
at least one memory storing program instructions executed by the at least one processor to perform operations comprising:
obtaining an initial image of a bone through the at least one network interface from the at least one server;
obtaining an initial location data structure containing data defining mapping between a set of locations on the surgical implant device and a corresponding set of locations relative to the bone in the initial image, through the at least one network interface from the at least one server;
obtaining a target image of the bone of the patient through the at least one network interface from the at least one server;
generating a transformation matrix that transforms a contour of a portion of the bone in the initial image to satisfy a defined rule for conforming to a contour of a corresponding portion of the bone in the target image;
generating a transformed location data structure based on applying the transformation matrix to the initial location data structure; and
displaying on the display device a graphical representation of the surgical implant device overlaid at locations on the target image of the bone determined based on the transformed location data structure.

17. The surgical implant planning computer of claim 16, wherein:
the surgical implant device comprises a surgical screw having a tip location and a tail location defined by the initial location data structure relative to the bone in the initial image; and
the generation of the transformed location data structure based on applying the transformation matrix to the initial location data structure, comprises scaling a distance between the tip and tail locations of the surgical screw defined relative to the bone in the target image based on the transformation matrix.

18. The surgical implant planning computer of claim 16, wherein the operations further comprise:
providing the transformed location data structure through the at least one network interface to a surgical robotic system to control positioning of a surgical end-effector of the surgical robotic system relative to a location on the bone of the patient based on data of the transformed location data structure.

19. A surgical system comprising:
a surgical implant planning computer comprising:
at least one network interface connected to at least one networked server;
a display device;
at least one processor connected to the at least one network interface and the display device; and
at least one memory storing program instructions executed by the at least one processor to perform operations comprising:
obtaining an initial image of a bone through the at least one network interface from the at least one server;
obtaining an initial location data structure containing data defining mapping between a set of locations on the surgical implant device and a corresponding set of locations relative to the bone in the initial image, through the at least one network interface from the at least one server;
obtaining a target image of the bone of the patient through the at least one network interface from the at least one server;
generating a transformation matrix that transforms a contour of a portion of the bone in the initial image to satisfy a defined rule for conforming to a contour of a corresponding portion of the bone in the target image;

generating a transformed location data structure based on applying the transformation matrix to the initial location data structure; and displaying on the display device a graphical representation of the surgical implant device overlaid at locations on the target image of the bone determined based on the transformed location data structure; and a surgical robotic system comprising:

a robotic arm configured to position a surgical end-effector; and a controller connected to the robotic arm, wherein the controller is configured to perform operations comprising:

transforming locations that are defined by the transformed location data structure in a reference coordinate system of the target image of the bone to another reference coordinate system of the surgical end-effector; and controlling movement of the surgical end-effector to position the surgical end-effector relative to a location on the bone of the patient based on the transformed locations to facilitate implantation of the surgical implant device in the bone of the patient.

20. The surgical system of claim 19, wherein:

the surgical implant device comprises a surgical screw having a tip location and a tail location defined by the initial location data structure relative to the bone in the initial image;

the operation of generating the transformed location data structure based on applying the transformation matrix to the initial location data structure, comprises scaling a distance between the tip and tail locations of the surgical screw defined relative to the bone in the target image based on the transformation matrix; and the operation of controlling movement of the surgical end-effector to position the surgical end-effector relative to a location on the bone of the patient based on the transformed locations to facilitate implantation of the surgical implant device in the bone of the patient.

\* \* \* \* \*